(12) United States Patent
Jensen

(10) Patent No.: US 11,739,370 B1
(45) Date of Patent: Aug. 29, 2023

(54) METHODS AND COMPOSITIONS FOR IN VIVO SCREENING OF THERAPEUTICS THROUGH SPATIAL TRANSCRIPTOMICS

(71) Applicant: GORDIAN BIOTECHNOLOGY, INC., San Francisco, CA (US)

(72) Inventor: Martin Borch Jensen, San Francisco, CA (US)

(73) Assignee: Gordian Biotechnology, Inc., San Francisco, CA (US)

( * ) Notice: Subject to any disclaimer, the term of this patent is extended or adjusted under 35 U.S.C. 154(b) by 5 days.

(21) Appl. No.: 17/144,046

(22) Filed: Jan. 7, 2021

Related U.S. Application Data

(60) Provisional application No. 62/959,699, filed on Jan. 10, 2020.

(51) Int. Cl.
| | | |
|---|---|---|
| *C12Q 1/6823* | (2018.01) | |
| *C12N 5/071* | (2010.01) | |
| *C12Q 1/6869* | (2018.01) | |

(52) U.S. Cl.
CPC ......... *C12Q 1/6823* (2013.01); *C12N 5/0602* (2013.01); *C12Q 1/6869* (2013.01); *C12Q 2563/185* (2013.01)

(58) Field of Classification Search
CPC ............... C12Q 1/6823; C12Q 1/6869; C12Q 2563/185; C12N 5/0602
See application file for complete search history.

(56) References Cited

U.S. PATENT DOCUMENTS

| | | |
|---|---|---|
| 2003/0044809 A1 | 3/2003 | Huylebroeck |
| 2012/0289581 A1 | 11/2012 | Chang |
| 2022/0073905 A1 | 3/2022 | Byrne et al. |

FOREIGN PATENT DOCUMENTS

| | | | |
|---|---|---|---|
| WO | WO 1996/038553 A1 | | 12/1996 |
| WO | WO 2010/111712 A2 | | 9/2010 |
| WO | WO 2011/150453 A1 | | 12/2011 |
| WO | WO 2013169917 | * | 11/2013 |
| WO | WO 2016/069591 A2 | | 5/2016 |
| WO | WO 2016138496 | * | 9/2016 |
| WO | WO 2017/040694 A2 | | 3/2017 |
| WO | WO 2020/097254 A1 | | 5/2020 |

OTHER PUBLICATIONS

Rodriques et al., Science, 363, 1463-1467, Mar. 2019.*
EP Extended Search Report in European Application No. 19881350, dated Jul. 19, 2022, 10 pages.
PCT International Search Report and Written Opinion in International Application No. PCT/US2022/26018, dated Aug. 9, 2022, 10 pages.
Wang et al., "Imaging-based pooled CRISPR screening reveals regulators of lncRNA localization", Proceedings of the National Academy of Sciences, May 2019, 116(22):10842-10851.
Wroblewska et al., "Protein Barcodes Enable High-Dimensional Single-Cell CRISPR Screens", Cell, Nov. 2018, pp. 1141-1155.

* cited by examiner

*Primary Examiner* — Cynthia B Wilder
(74) *Attorney, Agent, or Firm* — DLA Piper LLP (US)

(57) ABSTRACT

Provided herein are compositions and methods of use thereof for screening a plurality of uniquely identifiable therapeutic moiety in vivo by identifying one or more reporters indicative of a cell state.

18 Claims, 7 Drawing Sheets

METHODS AND COMPOSITIONS FOR IN VIVO SCREENING OF THERAPEUTICS THROUGH SPATIAL TRANSCRIPTOMICS

CROSS-REFERENCE TO RELATED APPLICATIONS

This application claims benefit of priority under 35 U.S.C. § 119(e) of U.S. Ser. No. 62/959,699, filed Jan. 10, 2020, the entire contents of which is incorporated herein by reference in its entirety.

BACKGROUND OF THE DISCLOSURE

Despite recent advancements, there remain a number of challenges in gene therapy and other types of clinical interventions, including translation of in vitro research into in vivo therapies, designing therapies when the disease etiology is unknown or not well understood, screening large numbers of interventions or therapy targets, and screening therapies in vivo to account for intracellular and extracellular factors that impact therapy design, safety, and/or efficacy. Therapies for aging related diseases or conditions can be complex due to multiple pathways and factors, including cellular and environmental factors, that contribute to the disease or condition, and/or involve poorly understood mechanisms. Due to the complexities of such diseases and conditions, efficacious therapies can be difficult to identify using standard screening paradigms.

SUMMARY OF THE DISCLOSURE

There is a need for more efficient and effective methods for screening and identifying novel therapies or interventions that address one or more challenges in the field.

The instant disclosure is based at least in part on discoveries that relate to enhancing the effectiveness of screening methods to identify candidate therapeutic moieties useful for treatment of a variety of diseases or conditions in a human or other animal. In particular, this disclosure relates to identifying effects of a possible therapeutic intervention in specific locations in an organoid or tissue. In various embodiments, the disclosure relates to administering to a biological entity (for example, an animal or an organoid) pooled expression cassettes having expressible therapeutic moieties and a therapeutic moiety barcode followed by spatial transcriptomics. Spatial transcriptomics, in some embodiments, may involves placing two-dimensional tissue slices on a coated surface (such as a glass slide) covered with 'surface probes' and subsequently initiating a reverse transcription reaction that will label mRNA molecules in the tissue slice with two barcodes comprising nucleotides, a first barcode identifying the individual mRNA molecule and a second barcode containing two-dimensional coordinates. This allows for subsequent reverse transcription, amplification, and next-generation sequencing of the tissue-derived cDNA, while preserving information about the original mRNA molecule and its location in the tissue. In some embodiments, an imaging step is performed before the reverse transcription step that can be used to correlate the spatial coordinates identified by the spatial barcode surface probes. Thus, the disclosure combines spatial transcriptomic readouts with pooled intervention libraries delivered by a vector (e.g., viral, non-viral, or the like) to a live animal or organoid. This may in some embodiments allow for measuring the effect of an intervention in not just the cell containing the intervention, but also in nearby and/or neighboring cells in the tissue. As used herein a "nearby cell" with regard to proximity of a cell from a cell containing an intervention, means a cell that is within 1 cm; 7.5 mm; or within 5.0 mm; or within 2.5 mm; or within 1 mm; or within 750 µm; or within 500 µm; or within 250 µm; or within 100 µm; or within 50 µm of a cell containing an intervention. In some embodiments a "nearby cell" as used herein is less than 1,000 cells; or less than 750 cells; or less than 500 cells; or less than 250 cells; or less than 100 cells, or less than 75 cells, or less than 50 cells; or less than 40 cells; or less than 30 cells; or less than 25 cells; or less than 20 cells; or less than 15 cells; or less than 10 cells; or less than 9 cells; or less than 8 cells; or less than 7 cells; or less than 6 cells; or less than 5 cells away from a cell containing an intervention. As used herein, a "neighboring cell" is a cell that is adjacent to a cell containing an intervention; or a cell that is adjacent to or within 2 cells from a cell containing and intervention; or a cell that is adjacent to or within 3 cells from a cell containing an intervention; or a cell that is adjacent to or within 4 cells from a cell containing and intervention; or a cell that is adjacent to or within 5 cells from a cell containing and intervention. A neighboring cell of the disclosure would also be a nearby cell; but it does not necessarily follow that a nearby cell would necessarily be a neighboring cell. The use of spatial transcriptomic readouts can enable libraries containing sequences which encode secreted peptides and other secreted factors, as therapeutic candidates. Such intervention libraries can be constructed with unique nucleotide barcodes, and DNA encoding a secreted factor. In certain embodiments, the methods and compositions of the instant disclosure allow for detection of an intervention when libraries are delivered to a live animal or organoid even where it is administered in a manner such that a low percentage of cells within the tissue receives an intervention. Tissue sections can, in some embodiments, be prepared for spatial transcriptomics. In addition to imaging the tissue for disease phenotypes, in situ hybridization may be used to identify cells with interventions, using probes targeting the unique nucleotide barcode describing intervention type, and fluorescent tags for imaging. As many current systems for single-cell sequencing suffer challenges due to 'drop out' resulting in individual mRNA molecules going undetected, the in-situ hybridization and spatial transcriptomics approach to identifying intervention-containing cells may add reliability compared to sequencing the nucleotide barcodes during single-cell sequencing where only a portion of the mRNA is captured.

The location of each intervention on the slide may, in some embodiments, be used to calculate a two-dimensional gradient map for each secreted factor. This gradient can be verified experimentally by staining the slide with fluorescently labeled antibodies targeting the individual secreted interventions, and/or using in situ hybridization probes for genes whose expression are increased by the secreted interventions. Sequencing the transcriptomes of cell clusters on the slide and comparing to baseline healthy and diseased transcriptomes thus allows testing whether proximity to cells secreting specific factors predicts alleviated disease states. These 2D slices can additionally be stacked using image processing softwares in order to generate a 3D image of the tissue, allowing mapping of diffused effects within the tissue. Such mapping can allow for understanding of effected cells in relation to their proximity to blood vessels, fatty deposits, or other external modifier. Such sequencing can additionally identify whether proximity to more than one factor is required for therapeutic effect, thereby identifying potential single or combination treatments. Where the disease has histologic manifestations, such as changes in cell size, shape, organelles etc., the transcriptomic signature of disease can be supplemented with histological analysis of regions near each type of intervention. In sum, various embodiments of this disclosure can allow screening for therapeutic effect of hundreds of secreted factors within a single animal/tissue, thus greatly improving efficiency relative to testing each factor in individual animals, while also testing for efficacy in a relevant in vivo environment rather than a reductionist cell culture model.

Accordingly, in a first aspect, provided is a method for identifying a candidate therapeutic moiety that includes:

(1) administering to an animal or an organoid a library of expression cassettes that can include: (a) a plurality of nucleic acid sequences, each encoding a different therapeutic moiety operably linked to a therapeutic moiety barcode; and (b) a plurality of nucleic acid sequences encoding one or more reporters that collectively, when expressed in a cell, are indicative of a cell state or a likelihood of a cell state of the cell;

(2) removing a tissue from said animal or organoid and placing a two-dimensional section of said tissue on coated surface; wherein the coating comprises oligo(dT) primers and/or primers matching specific sequences of interest, encoding a spatial barcode providing coordinates for each of various spots on said coated surface;

(3) identifying a candidate therapeutic moiety that results in the change in cell state or likelihood of a cell state of one or more cells of the animal or the organoid; and coordinating the presence of the therapeutic moiety to a specific cell or location within the tissue section using the spatial barcode.

In some embodiments, the tissue is permeabilized on the coated surface. In some embodiments, reverse transcription is performed on the tissue section to produce cDNA. In some embodiments, RNA sequencing is performed on the tissue section following the generation of cDNA through reverse transcription. In some embodiments, primers and spatial barcodes are linked directly to the glass surface, or to another material coating the glass surface. In some embodiments, primers and spatial barcodes are linked directly to beads which are attached to the glass surface (see for example, Rodrigues Et Al, Science 363:6434, pp 1463-1467.). In certain embodiments, the primers or barcodes are bound directly to a glass surface or a material on the glass surface using polymer linkers. In certain embodiments, the primers or barcodes are bound directly to a glass surface or a material on the glass surface using peptide or protein linkers. In certain embodiments, the primers or barcodes are bound directly to a glass surface or a material on the glass surface using Click-chemistry linkers. In certain embodiments, the primers or barcodes are bound directly to a glass surface or a material on the glass surface using nucleotide linkers which are not themselves primers.

Accordingly, in a second aspect, provided is a method for identifying a candidate therapeutic moiety that includes:

(1) administering to an animal or an organoid a library of expression cassettes that include: (a) a plurality of nucleic acid sequences, each encoding a different therapeutic moiety operably linked to a therapeutic moiety barcode; and (b) a plurality of nucleic acid sequences encoding one or more reporters that collectively, when expressed in a cell, are indicative of a cell state or a likelihood of a cell state of the cell;

(2) removing a tissue from said animal or organoid and placing a two-dimensional section of said tissue on a coated surface; wherein the coating comprises oligo(dT) primers encoding a spatial barcode providing coordinates for each of various spots on said coated surface;

(3) permeabilizing the tissue on the slide;

(4) performing reverse transcription in said tissue section in situ to produce cDNA;

(5) performing RNA sequencing using the cDNA;

(6) identifying a candidate therapeutic moiety that results in the change in a cell state or likelihood of a cell state of one or more cells of the animal or the organoid; and coordinating the presence of the therapeutic moiety to a specific cell or location within the tissue section using the spatial barcode.

Further, in a third aspect, provided is a method for identifying a candidate therapeutic moiety that includes:

(1) administering to an animal or an organoid a library of expression cassettes that include: (a) a plurality of nucleic acid sequences, each encoding a different therapeutic moiety operably linked to a therapeutic moiety barcode; and (b) a plurality of nucleic acid sequences encoding one or more reporter constructs that collectively, when expressed in a cell, are indicative of a cell state or a likelihood of a cell state of the cell;

(2) removing a tissue from said animal or organoid and placing a two-dimensional section of said tissue on a coated surface; wherein the coating comprises primers encoding a spatial barcode providing coordinates for each of various spots on said coated surface;

(3) identifying the location of therapeutic moieties through combined detection of therapeutic moiety barcodes and spatial barcodes;

(4) detecting a change in a cell state or likelihood of a cell state of one or more cells of the animal or the organoid using one or more selected from the group consisting of reporter constructs, histology, and transcriptomic analysis;

(5) performing a weighted probability analysis to predict the likelihood of a cell state based on the cell's proximity to one or more therapeutic moieties in the tissue, thereby identifying a candidate therapeutic moiety.

In certain embodiments, a method for identifying a candidate therapeutic moiety of the disclosure includes: (1) administering to an animal or an organoid a library of expression cassettes that include: (a) a plurality of nucleic acid sequences, each encoding a different therapeutic moiety operably linked to a therapeutic moiety barcode; and (b) a plurality of nucleic acid sequences encoding one or more reporter constructs that collectively, when expressed in a cell, are indicative of a cell state or a likelihood of a cell state of the cell; (2) removing a tissue from said animal or organoid and placing a two-dimensional section of said tissue on a coated surface; wherein the coating comprises primers encoding a spatial barcode providing coordinates for each of various spots on said coated surface; (3) identifying the location of therapeutic moieties through combined detection of therapeutic moiety barcodes and spatial barcodes; (4) detecting a change in a cell state or likelihood of a cell state of one or more cells of the animal or the organoid using a combination of reporter constructs, histology, and transcriptomic analysis; and (5) performing a weighted probability analysis to predict the likelihood of a cell state based on the cell's proximity to one or more therapeutic moieties in the tissue, thereby identifying a candidate therapeutic moiety.

In some embodiments of the methods provided herein, the change in the cell state or a likelihood of the cell state correlates to a therapeutic effect resulting from the candidate therapeutic moiety. In certain embodiments, the likelihood of the cell state correlates with a level of protein or oligonucleotide expression in the cell.

The term "two-dimensional section" as used herein, refers to a section or slice of tissue. For example, a slice or section of tissue commonly used in routine histology. In some embodiments, the two-dimensional section has a thickness between 1-20 µm. In some embodiments, the two-dimensional section has a thickness between 2-18 µm. In some embodiments, the two-dimensional section has a thickness between 5-15 µm.

In some embodiments of the methods provided herein, the therapeutic moiety encodes for either a secreted or cell-intrinsic signaling molecule involved in cell-cell signaling.

In some embodiments of the methods provided herein, the RNA sequencing method includes spatial transcriptomics. In some embodiments, the identifying step includes performing spatial transcriptomic RNA sequencing of a population of cells to determine an amount of the candidate therapeutic moiety present in the population of cells.

In certain embodiments, the approximate cell location in combination with the presence of a candidate therapeutic moiety allows understanding of the intervention's effect on all the cells contained within the specific spot, or adjacent spots, on the slide.

In some embodiments, of the aspects and embodiments provided herein each expression cassette is packaged in a virus. In some embodiments, each expression cassette is a non-viral vector or vehicle for delivery. In some embodiments, a non-viral vector is: a linear vector, a plasmid, a polymer-based vector, or a transposon. In some embodiments, a library of any embodiment disclosed herein is delivered as a nanoparticle, a lipid nanoparticle, an RNA nanoparticle, or an exosome. In some embodiments, a library of any embodiment is formulated for delivery using a physical method, a needle, a ballistic DNA, electroporation, sonoporation, photoporation, magnetofection, or hydroporation, or is formulated for delivery with a chemical carrier, an inorganic particle, a metal nanoparticle, a magnetic nanoparticle, a lipid, a lipid nanoparticle, a peptide, a polymer, polyethylenimine (PEI), chitosan, polyester, dendrimer, or polymethacrylate. In some embodiments, the virus is an AAV, an adenovirus, or a lentivirus. In some embodiments, a plurality of expression cassettes comprises at least 10, 50, 100, 500 or 1000 different expression cassettes. In some embodiments, a plurality of expression cassettes encodes at least 10, 50, 100, 500, 1000, or 10000 different therapeutic moieties. In some embodiments, a therapeutic moiety is a DNA or RNA sequence, shRNA, siRNA, miRNA, antisense oligonucleotide, morpholino, protein degradation tag, a product of a therapeutic transgene, a gene editing complex, a Cas fusion protein, CRISPRi, CRISPRa, RNA editing element, a regulatory element of RNA splicing, RNA degradation element, or an epigenetic modification element. In some embodiments, a therapeutic moiety is a shRNA. In some embodiments, a therapeutic moiety is a siRNA. In some embodiments, a therapeutic moiety is a product of a therapeutic transgene. In some embodiments, a therapeutic moiety is a Cas fusion protein. In some embodiments, each therapeutic moiety barcode differs from the other therapeutic moiety barcodes by at least 1, 2, 3, 4, 5, 6, 7, 8, 9, or 10 bases. In some embodiments, a therapeutic moiety barcode disclosed herein is a nucleic acid sequence comprising at least 2, 3, 4, 5, 6, 7, 8, 9, or 10 bases. In some embodiments, the therapeutic moiety barcode is located in an open reading frame of a therapeutic moiety disclosed herein. In some embodiments, transcription of a therapeutic moiety barcode is linked to transcription of the therapeutic moiety. In some embodiments, a library comprises nucleic acid sequences encoding two or more reporters. In some embodiments, the nucleic acid sequences encoding each reporter is operably linked to a promoter. In some embodiments, a promoter further comprises an enhancer. In some embodiments, reporters disclosed herein can be a selection marker, a detectable protein or oligonucleotide, a cell surface marker, a drug-sensitive element, an inducible element, or a fluorescent protein. In some embodiments, a fluorescence signal from the fluorescent protein correlates to a likelihood of the cell state or a change from one cell state to a second cell state. In some embodiments, an amount or a count of the reporters in a population of cells greater than random distribution is indicative of the likelihood of the cell state in the population of cells. In some embodiments, such greater than random distribution is statistically significant. In some embodiments, the nucleic acid sequence encoding each reporter is no more than 4000, 3500, 3000, 2500, 2000, 1500, 1400, 1300, 1200, 1100, 1000, 900, 800, 700, 600, 500, 400, 300, 200, or 100 bp. In some embodiments, the nucleic acid sequence encoding each reporter is 700-1000 bp or 1000-2000 bp. In some embodiments, the promoter is no more than 100, 150, 200, 250, 300, 350 bp, 400 bp, 450 bp, or 500 bp. In some embodiments, the cell state is a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, or a non-cancerous cell state, a hyperplastic state, a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state, or any combination thereof. In some embodiments, the cell state is a state in which the cell has, is characterized by, or is associated with a disease or a condition, e.g., an age-related disease or condition. In some embodiments, one or more reporters disclosed herein are capable of differentiation between different cell states. In some embodiments, the differentiation comprises a change in a cellular parameter, a cellular activity or function, cell physiology, cell size, cell morphology, cell shape, cell marker, cell shape, or cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof resulting from a therapeutic moiety in the cell. In some embodiments, the cellular activity or function comprises transfection, transcription, replication, protein expression, epigenetic modification, cell marker expression, interaction with an exogenous molecule, or any combination thereof. In some embodiments, the differentiation is between a diseased cell and a healthy cell, or between an abnormal cell and a normal cell. In some embodiments, the disease or the condition is an age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic steatohepatitis, idiopathic pulmonary fibrosis, sarcopenia, a neurological condition, Alzheimer's disease, or dementia, or wherein the disease or the condition is associated with senescence, inadequate or imbalanced replication activity, altered secretory phenotype, altered neuronal signaling, abnormal immunological activity, undifferentiated cell state, or cancerous. In some embodiments, the therapeutic moiety and the reporters are encoded on the same expression cassette. In some embodiments, the therapeutic moiety and the reporters are encoded on different expression cassettes. In some embodiments, expression of the reporters is operably linked to an inducible transcriptional element responsive to or linked to a transcription factor, recombinase or other activator in the expression cassettes comprising the therapeutic moieties, or wherein expression of the reporters is linked to expression of the therapeutic moieties. In some embodiments, the activator is Gal4, cre, or FLP.

In some embodiments, each expression cassette of the plurality of expression cassettes is packaged in a virus, wherein the virus is adeno-associated virus (AAV), adenovirus, or lentivirus.

In certain embodiments of the methods provided herein, each of the spots on the slide includes 1-100 cells; or 1-50 cells; or 1-25 cells; 1-10 cells; or 1-5 cells; or 5-50 cells; or 5-25 cells; or 5-10 cells; or 10-100 cells; or 10-75 cells; or 10-50 cells; or 10-25 cells; or 10-20 cells; or about 1 cell; or about 2 cells; or about 5 cells; or about 10 cells; or about 20 cells; or about 25 cells; or about 50 cells; or about 75 cells; or about 100 cells.

In some embodiments, the cell state is a healthy cell state, a non-diseased cell state, or a normal cell state. In some embodiments, the change in the cell state or a likelihood of the cell state correlates to a therapeutic effect resulting from the candidate therapeutic moiety. In some embodiments, the identifying comprises identifying the candidate therapeutic moiety based on a presence of the therapeutic moiety barcode in the cell. In some embodiments, the likelihood of the cell state correlates with a level of protein or oligonucleotide expression in the cell. In some embodiments, the level of protein or oligonucleotide expression is measured using a histological or fluorescent staining method. In some embodiments, the different therapeutic moieties are selected from the group consisting of: DNA, RNA, shRNA, siRNA, miRNA, an antisense oligonucleotide, a morpholino, a protein degradation tag, a product of a transgene, a gene editing complex, a Cas fusion protein, CRISPRi, CRISPRa, an RNA editing element, a regulatory element of RNA splicing, an RNA degradation element, an epigenetic modification element, and any combination thereof. In some embodiments, the different therapeutic moieties are products of transgenes. In some embodiments, the different therapeutic moieties are shRNA. In some embodiments, each expression cassette in the library of expression cassettes is packaged in an expression vector. In some embodiments, the expression vector is a virus. In some embodiments, the virus is an adeno-associated virus (AAV), an adenovirus, or a lentivirus.

In another aspect, a candidate therapeutic moiety identified by the method of any one of the preceding is provided.

In another aspect, a biological entity comprising a plurality of cells is provided, each of the plurality of cells expressing: a different therapeutic moiety operably linked to a therapeutic moiety barcode; and one or more reporters that collectively, when expressed in a cell, are indicative of a cell state or a likelihood of a cell state of the cell. In some embodiments, the biological entity is an animal or an organoid. In some embodiments, the different therapeutic moieties are selected from the group consisting of: DNA, RNA, shRNA, a product of a transgene, a gene editing complex, a Cas fusion protein, CRISPRi, CRISPRa, an RNA editing element, siRNA, miRNA, an antisense oligonucleotide, a morpholino, a protein degradation tag, a regulatory element of RNA splicing, an RNA degradation element, an epigenetic modification element, and any combination thereof. In some embodiments, the biological entity is a disease model.

Further provided herein are compositions and methods of use thereof for screening a library of therapeutics or clinical interventions in vivo, e.g., a library comprising a plurality of therapeutic moieties in vivo. In various embodiments, such methods of in vivo screening are high throughput, comprising RNA sequence analysis. In some embodiments, high throughput in vivo screening involves one or more in vitro assays, e.g., detecting one or more reporters associated with a cell state, fluorescence staining, nucleic acid hybridization assays, protein assay, antibody-based assay, RNA assay, etc. In some embodiments, a high throughput screen or method of use thereof further comprises one or more reporters which can indicate a cell state or a change in cell state, such as from a diseased cell to a healthy cell or to an improved cell state. Such change from one cell state to a different cell state provides a therapeutic index that allows one to screen for, identify, improve, or make/design novel therapeutic moieties or therapies that are known to result in the desired alteration or change in cell state in vivo.

The present disclosure contemplates a library comprising a plurality of expression cassettes, each comprising: a nucleic acid sequence encoding for a different therapeutic moiety (e.g., a DNA element, an RNA element, a therapeutic transgene, or a nucleic acid sequence that encodes a protein) operably linked to a therapeutic moiety barcode and one or more reporters that collectively are indicative of a likelihood of a cell state of a cell. In some embodiments, the likelihood of the cell state is statistically significantly greater than random distribution. In some embodiments, the likelihood of the cell state is at least 50%, 55%, 60%, 65%, 70%, 75%, 80%, 85%, 90%, 95%, or 100%. In some embodiments, the likelihood of the cell state is relative to a control, such as an expression cassette without any therapeutic moiety, or an empty vector.

In some aspects, the present disclosure contemplates a biological entity (e.g., an animal or organoid) comprising a library described herein. In some embodiments, the library comprises at least 10, 50, 100, 500, or 1000 different expression cassettes, each encoding a different therapeutic moiety. In some embodiments, the biological entity is a disease model. In some embodiments, the biological entity is an animal, and the animal is a mammal, a humanized mammal, or a mouse. In some embodiments, the biological entity is a cell or a population of cells, a tissue, or an organoid. In some embodiments, the biological entity is characterized as having or is a model for a disease or condition. In some embodiments, the disease or condition is an age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic steatohepatitis, idiopathic pulmonary fibrosis, sarcopenia, a neurological condition, Alzheimer's disease, or dementia.

In some aspects, the present disclosure contemplates a method for identifying a candidate therapeutic moiety comprising: administering into a biological entity a library of any embodiment disclosed herein, and identifying a candidate therapeutic moiety that results in a change in a cell state or a likelihood of a cell state. In some embodiments, the cell state is a healthy cell state, a non-diseased cell state, or a normal cell state. In some embodiments, the change in the cell state or a likelihood of the cell state correlates to a therapeutic effect resulting from the therapeutic moiety. In some embodiments, the identifying comprises RNA sequencing, spatial transcriptomics, bulk analysis, or sequencing a population of cells to determine an amount or presence of the therapeutic moieties present in the population of cells. In some embodiments, the likelihood of the cell state correlates with a level of protein or oligonucleotide expression in the cell. In some embodiments, the level of protein or oligonucleotide expression is measured using a histological or a staining method, such as a fluorescent staining method.

In some aspects, the present disclosure contemplates a reporter construct comprising a promoter operably linked to a nucleic acid sequence encoding one or more reporters. In some embodiments, the likelihood of the cell state correlates with a level of protein or oligonucleotide expression in the cell. In some embodiments, the level of protein or oligonucleotide expression is measured using a histological or staining method, such as a fluorescent staining method. In some embodiments, the promoter is a cognate promoter of a gene known to be downregulated or upregulated in the cell state. In some embodiments, the nucleic acid sequence encoding the one or more reporters is operably couples to two or more promoters. In some embodiments, the reporter further comprises two or more different reporters. In some embodiments, the promoter further comprises an enhancer. In some embodiments, each of the reporters is a different detectable protein or oligonucleotide, a different selection marker, a different fluorescent protein, or a different cell surface marker, or any combination thereof. In some embodiments, each reporter is a detectable protein, a selection marker, a fluorescent protein, or a cell surface marker. In some embodiments, expression of the one or more reporters is operably linked to a transcriptional inducer or transcriptional activator associated with a therapeutic moiety, such that expression of the therapeutic moiety induces or activates expression of the reporters. In some embodiments, detecting the reporters allows for differentiation between different cell states. In some embodiments, a fluorescence signal from the reporters correlates to the likelihood of the cell state, allowing for differentiation between different cell states. In some embodiments, the differentiation is between a diseased cell state and a healthy cell state, or between an abnormal cell state and a normal cell state. In some embodiments, the differentiation is based on a fluorescence ratio between different reporters or based on an amount of reporters expressed in a population of cells. In some embodiments, the differentiation between different cell states comprises a change in a cellular parameter, a cellular activity or function, cell physiology, cell size, cell morphology, cell shape, cell marker, cell shape, or cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof resulting from expression of the therapeutic moiety in the cell. In some embodiments, the differentiation is measured by detecting or counting the reporters in a population of cells. In some embodiments, the cellular parameter comprises a cellular activity or function, cell physiology, cell size, cell morphology, cell shape, cell marker, cell density, or any combination thereof. In some embodiments, the differentiation correlates to a therapeutic index. In some embodiments, the ratio between the different reporters or different fluorescent proteins or the amount of reporters expressed in a population of cells correlates to a therapeutic index, indicative of a therapeutic effect resulting from a therapeutic moiety expressed in the cell. In some embodiments, the therapeutic index is based on a change in a cellular parameter, a cellular activity or function, cell physiology, cell size, cell morphology, cell shape, cell marker, or cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof between different cell states. In some embodiments, the cell state is a disease or a condition. In some embodiments, the disease or the condition is age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease, or dementia. In some embodiments, the disease or the condition is associated with senescence, inadequate or imbalanced replication activity, altered secretory phenotype, altered neuronal signaling, abnormal immunological activity, undifferentiated cell state, or cancerous. In some embodiments, the cell state is: a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, or a non-cancerous cell state, a hyperplastic state, a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state. In some embodiments, the likelihood of the cell state is statistically significantly greater than random distribution, or wherein the likelihood of the cell state is at least 50%, 55%, 60%, 65%, 70%, 75%, 80%, 85%, 90%, 95%, or 100%. In some embodiments, the cell state comprises at least 5%, 10%, 20%, 30%, 40%, 50%, 60%, 70%, 80%, or 90% improvement or amelioration relative to a diseased state, as measured by the cell's cellular parameter, cell physiology, transcriptomic profile, proteomic profile, metabolomic profile, epigenomic profile, proteogenomic profile, immunoproteomic profile, pharmacogenomic profile, or nucleomic profile relative to a diseased state, or as measured by the reporters. In some embodiments, the nucleic acid sequence encoding a reporter is no more than 4000, 3500, 3000, 2500, 2000, 1500, 1400, 1300, 1200, 1100, 1000, 900, 800, 700, 600, 500, 400, 300, 200, or 100 bp. In some embodiments, the promoter is no more than 50, 100, 150, 200, 250, 300, 350, 400 bp, 450 bp, or 500 bp. In some embodiments, a reporter construct further comprises a nucleic acid sequence encoding one or more therapeutic moieties. In some embodiments, each of the therapeutic moieties is linked to a transcription factor that interacts with an inducible transcriptional element associated with the reporters. In some embodiments, the activator is Gal4, cre, or FLP.

In some aspects, a biological entity comprises a reporter construct described herein. In some embodiments, the biological entity is a disease model. In some embodiments, the biological entity is an animal, and the animal is a mammal, a humanized mammal, or a mouse. In some embodiments, the biological entity is a cell or a population of cells, a tissue, or an organoid. In some embodiments, the biological entity is characterized as having or be a model for a disease or condition. In some embodiments, the disease or condition is an age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease, or dementia. In some embodiments, the disease or the condition is associated with senescence, inadequate or imbalanced replication activity, altered secretory phenotype, altered neuronal signaling, abnormal immunological activity, undifferentiated cell state, or cancerous.

In some aspects, a method of identifying a candidate therapeutic moiety comprises administering into a biological entity a reporter construct disclosed herein and a library of therapeutic moieties, and identifying a candidate therapeutic moiety that results in a change in a cell state. In some embodiments, the cell state is: a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, or a non-cancerous cell state, a hyperplastic state, a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state. In some embodiments, the change in the cell state correlates to a therapeutic effect. In some embodiments, the therapeutic effect comprises a change in a cellular parameter, a cellular activity or function, cell physiology, cell size, cell morphology, cell shape, cell marker, or cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof resulting from a therapeutic moiety expressed in a cell. In some embodiments, the identifying comprises bulk analysis sequencing, RNA sequencing, sequencing for an amount of a therapeutic moiety or a therapeutic moiety barcode in a population of cells, a histological assay, a staining assay, or a fluorescent staining assay.

In aspects, the present disclosure contemplates a kit comprising a plurality of therapeutic expression cassettes, each comprising a nucleic acid encoding a different therapeutic moiety operably linked to a therapeutic moiety barcode and a transcriptional activator or an inducer molecule, and a plurality of reporter expression cassettes, each comprising an inducible transcriptional element linked to a nucleic acid sequence encoding a reporter. In some embodiments, the transcriptional activator or inducer molecule in each therapeutic expression cassette interacts with, activates, or induces the inducible transcriptional element in each reporter expression cassette, such that expression of the reporter is operably linked to expression of the therapeutic moiety. In some embodiments, the reporters comprise one or more selection markers. In some embodiments, the reporters comprise one or more detectable proteins, fluorescent proteins, cell surface markers, drug-sensitive elements, or inducible transcriptional elements. In some embodiments, expression of the reporter is operably linked to a promoter. In some embodiments, the promoter further comprises an enhancer. In some embodiments, the plurality of therapeutic expression cassettes comprises at least 10, 50, 100, 500 or 1000 different therapeutic expression cassettes. In some embodiments, the plurality of therapeutic expression cassettes comprises at least 10, 50, 100, 500, 1000, or 10000 different therapeutic moieties. In some embodiments, the therapeutic moieties comprise a DNA sequence, an RNA sequence, a shRNA, siRNA, miRNA, antisense oligonucleotide, morpholino, protein degradation tag a therapeutic transgene, or a gene editing complex. In some embodiments, the therapeutic moieties comprise a Cas fusion protein, CRISPRi, CRISPRa, RNA editing element, a regulatory element of RNA splicing, RNA degradation element, or an epigenetic modification element. In some embodiments, the therapeutic moieties comprise a shRNA. In some embodiments, the therapeutic moieties comprise a siRNA. In some embodiments, the therapeutic moieties comprise the product of a therapeutic transgene. In some embodiments, the therapeutic moieties comprise a Cas fusion protein. In some embodiments, each therapeutic moiety barcode differs from the other therapeutic moiety barcodes by at least 1, 2, 3, 4, 5, 6, 7, 8, 9, or 10 bases. In some embodiments, the therapeutic moiety barcode is a nucleic acid sequence comprising at least 2, 3, 4, 5, 6, 7, 8, 9, 10, 11, 12, 13, 14, 15, 16, 17, 18, 19 or 20 bases. In some embodiments, the therapeutic moiety barcode is a nucleic acid sequence having between 1 and 20 bases; or 4 and 20 bases; or 4 and 10 bases; or 1 and 12 bases; or 2 and 11 bases. In some embodiments, the therapeutic moiety barcode is a nucleic acid sequence comprising at least 10 bases; or at least 11 bases; or at least 12 bases; or at least 13 bases; or at least 14 bases; or at least 15 bases; or at least 16 bases; or at least 17 bases; or at least 18 bases; or at least 19 bases; or at least 20 bases. In some embodiments, the therapeutic moiety barcode is located in an open reading frame of the therapeutic moiety, or transcription of the therapeutic moiety barcode is linked to transcription of the therapeutic moiety. In some embodiments, expression of the reporters is indicative of expression of the therapeutic moiety in the cell. In some embodiments, the activator is Gal4, cre, or FLP. In some embodiments, the therapeutic expression cassettes comprise viral vectors or non-viral vectors. In some embodiments, the selection expression cassettes are viral vectors or non-viral vectors. In some embodiments, the therapeutic expression cassettes and the reporter expression cassettes are mixed together in one sample or supplied as separate samples. In some embodiments, the viral vectors comprise AAV, adenovirus, or lentivirus. In some embodiments, the non-viral vectors comprise a linear vector, a plasmid, a polymer-based vector, or a transposon, or is delivered as a nanoparticle, a lipid nanoparticle, an RNA nanoparticle, or an exosome, or is formulated for delivery using a physical method, a needle, a ballistic DNA, electroporation, sonoporation, photoporation, magnetofection, or hydroporation, or is formulated for delivery with a chemical carrier, an inorganic particle, a metal nanoparticle, a magnetic nanoparticle, a lipid, a lipid nanoparticle, a peptide, a polymer, polyethylenimine (PEI), chitosan, polyester, dendrimer, or polymethacrylate.

In some aspects, a method for identifying a candidate therapeutic moiety comprises administering into a biological entity, the contents of a kit disclosed herein (e.g., a library of expression cassettes), and identifying a candidate therapeutic moiety that results in a change in a cell state. In some embodiments, the cell state is: a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, or a non-cancerous cell state, a hyperplastic state, a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state. In some embodiments, the change in the cell state correlates to a therapeutic effect. In some embodiments, the therapeutic effect comprises a change in a cellular parameter, a cellular activity or function, cell physiology, cell size, cell morphology, cell shape, cell marker, or cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof resulting from a therapeutic moiety expressed in a cell. In some embodiments, the identifying comprises bulk analysis, sequencing, RNA sequencing, sequencing for an amount or strength of a therapeutic moiety or a therapeutic moiety barcode in a population of cells, a histological assay, or a staining assay, e.g., a fluorescent staining assay.

In some embodiments, the in vivo screening comprises administering a library of therapeutic moieties to a biological entity. In some embodiments, the administering comprises local injection or systemic injection or infusion. In some embodiments, the biological entity is characterized as having or as a model for an age-related disease or condition, a liver disease or condition, a metabolic disease, a cardiovascular disease, a neurodegenerative disease or condition, an eye disease or condition, a degenerative disease or condition, a type of arthritis, non-alcoholic fatty liver disease, non-alcoholic steatohepatitis, liver cirrhosis, idiopathic pulmonary fibrosis, sarcopenia, a neurological condition, Alzheimer's disease, or dementia, or a disease or condition associated with senescence, inadequate or imbalanced replication activity, altered secretory phenotype, altered neuronal signaling, abnormal immunological activity, undifferentiated cell state, or cancerous. In some embodiments, the cell state is a disease or a condition, or wherein the cell state is a diseased cell state, a healthy cell state, a senescent cell state, a metastatic state, a non-metastatic state, an apoptotic cell state, a non-apoptotic cell state, an infectious cell state, a non-infectious cell state, a hyperplastic state, or a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state, or wherein the cell state is associated with senescence, impaired cellular function, inadequate or imbalanced replication activity, an altered secretory phenotype, altered neuronal signaling, abnormal immunological activity, mis-differentiated cell, undifferentiated cell, or cancer. In some embodiments, the plurality of different therapeutic moieties comprises at least 10, 20, 50, 100, 500, or 1000 different therapeutic moieties. In some embodiments, the therapeutic moieties comprise DNA, RNA, shRNA, a product of a therapeutic transgene, gene editing proteins, a Cas fusion protein, CRISPRi, CRISPRa, RNA editing element, a regulatory element of RNA splicing, RNA degradation element, or an epigenetic modification element. In some embodiments, the method further comprises two or more reporters. In some embodiments, expression of the reporters is driven by a promoter. In some embodiments, the promoter further comprises an enhancer. In some embodiments, the promoter is derived from a cognate promoter of a gene known to be associated with a disease or condition. In some embodiments, the reporters are selection markers, detectable proteins, fluorescent proteins, drug-sensitive elements, inducible transcriptional elements, or cell surface markers. In some embodiments, the reporters are different fluorescent proteins. In some embodiments, the reporters produce fluorescence signals that allow for differentiation between different cell states in the animal. In some embodiments, the identifying comprises measuring a change in a cellular parameter, cell physiology, transcriptomic profile, proteomic profile, metabolomic profile, epigenomic profile, proteogenomic profile, immunoproteomic profile, pharmacogenomic profile, or nucleomic profile, or any combination thereof resulting from the therapeutic moiety. In some embodiments, the cell state is: a disease or a condition, or wherein the cell state is a diseased cell state, a healthy cell state, a senescent cell state, a metastatic state, a non-metastatic state, an apoptotic cell state, a non-apoptotic cell state, an infectious cell state, a non-infectious cell state, a hyperplastic state, or a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state, or wherein the cell state is associated with senescence, impaired cellular function, inadequate or imbalanced replication activity, an altered secretory phenotype, altered neuronal signaling, abnormal immunological activity, mis-differentiated cell, undifferentiated cell, or cancer. In some embodiments, the cellular parameter or physiology comprises cell size, shape, or density. In some embodiments, bulk sequencing comprises sequencing for a therapeutic moiety or a therapeutic moiety barcode in a population of cells. In some embodiments, abundance of the therapeutic moiety in the population of cells is indicative of a therapeutic effect associated with the therapeutic moiety. In some embodiments, the promoter is identified using one or more machine learning methods, statistical methods, a neural network, differential co-expression network, interaction network, an eigengene network, clustering, or gene set analysis, or any combination thereof. In some embodiments, the machine learning methods further comprise modules of genes co-expressed or differentially expressed in different cell states.

In some embodiments, the therapeutic effect comprises a change in the cell state, wherein the change is at least 5%, 10%, 20%, 30%, 40%, 50%, 60%, 70%, 80%, or 90% reduction in a disease cell state or at least 5%, 10%, 20%, 30%, 40%, 50%, 60%, 70%, 80%, or 90% increase in the likelihood of a healthy cell state, or wherein the change is at least 5%, 10%, 20%, 30%, 40%, 50%, 60%, 70%, 80%, or 90% increase in cellular repair or regeneration. In some embodiments, the cell state is: a disease or a condition, or wherein the cell state is a diseased cell state, a healthy cell state, a senescent cell state, a metastatic state, a non-metastatic state, an apoptotic cell state, a non-apoptotic cell state, an infectious cell state, a non-infectious cell state, a hyperplastic state, or a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state, or wherein the cell state is associated with senescence, impaired cellular function, inadequate or imbalanced replication activity, an altered secretory phenotype, altered neuronal signaling, abnormal immunological activity, mis-differentiated cell, undifferentiated cell, or cancer. In some embodiments, the RNA sequencing uses one or more barcode sequences, which may be amplified prior to or during sequencing. In some embodiments, the therapeutic moiety barcode sequences are unique to each therapeutic moiety. In some embodiments, each therapeutic moiety barcode sequence is a nucleic acid sequence of at least 2, 3, 4, 5, 6, 7, 8, 9, 10, or more than 10 bases. In some embodiments, the therapeutic moieties are engineered based on transcriptomic signatures of a disease or a condition, or engineered based on a machine learning method, a statistical method, a neural network, a differential co-expression network, an eigengene network, an interaction network, clustering, or gene set analysis. In some embodiments, the transcriptomic signatures further comprise a neural network of modules of co-regulated genes associated with a disease state. In some embodiments, the reporters comprise selection markers, detectable proteins, fluorescent proteins, drug-sensitive elements, inducible transcriptional elements, or cell surface markers. In some embodiments, the method further comprises analyzing a cellular parameter, cell physiology, transcriptomic profile, proteomic profile, metabolomic profile, epigenomic profile, proteogenomic profile, immunoproteomic profile, pharmacogenomic profile, or nucleomic profile, or any combination thereof of the cells with the therapeutic effect relative to a healthy cell. In some embodiments, the method further comprises using a machine learning method, a statistical method, a neural network, a differential co-expression network, an eigengene network, an interaction network, a clustering, or a gene set analysis to modify a therapeutic moiety identified from the in vivo screen. In some embodiments, the method further comprises combining two or more therapeutic moieties identified from the in vivo screen.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the case of conflict, the specification, including definitions, will control.

BRIEF DESCRIPTION OF THE DRAWINGS

Some novel features various aspect and embodiments of this disclosure are set forth with particularity in the appended claims. A better understanding of the features and advantages of the present aspect and embodiments can be obtained by reference to the following detailed description that sets forth illustrative embodiments, in which the principles of the invention are utilized, and the accompanying drawings of which:

DETAILED DESCRIPTION OF THE DISCLOSURE

Introduction

The prevalence of a number of diseases or conditions increases exponentially with age, such as after the age of 65 years. Various age-related diseases or conditions include, but are limited to, Alzheimer's disease, muscle wasting, reduced bone density, cancer, cardiovascular disease, dementia, diabetes, and other degenerative diseases. The fraction of the population in old age is rising sharply globally and in the United States. There is a need for unbiased in vivo screening of a plurality of therapeutic moieties earlier during drug discovery or development, such that multiple parameters and aspects of a therapy can be screened at the same time and/or within the same biological entity (e.g., an animal or organoid).

Figure 1:
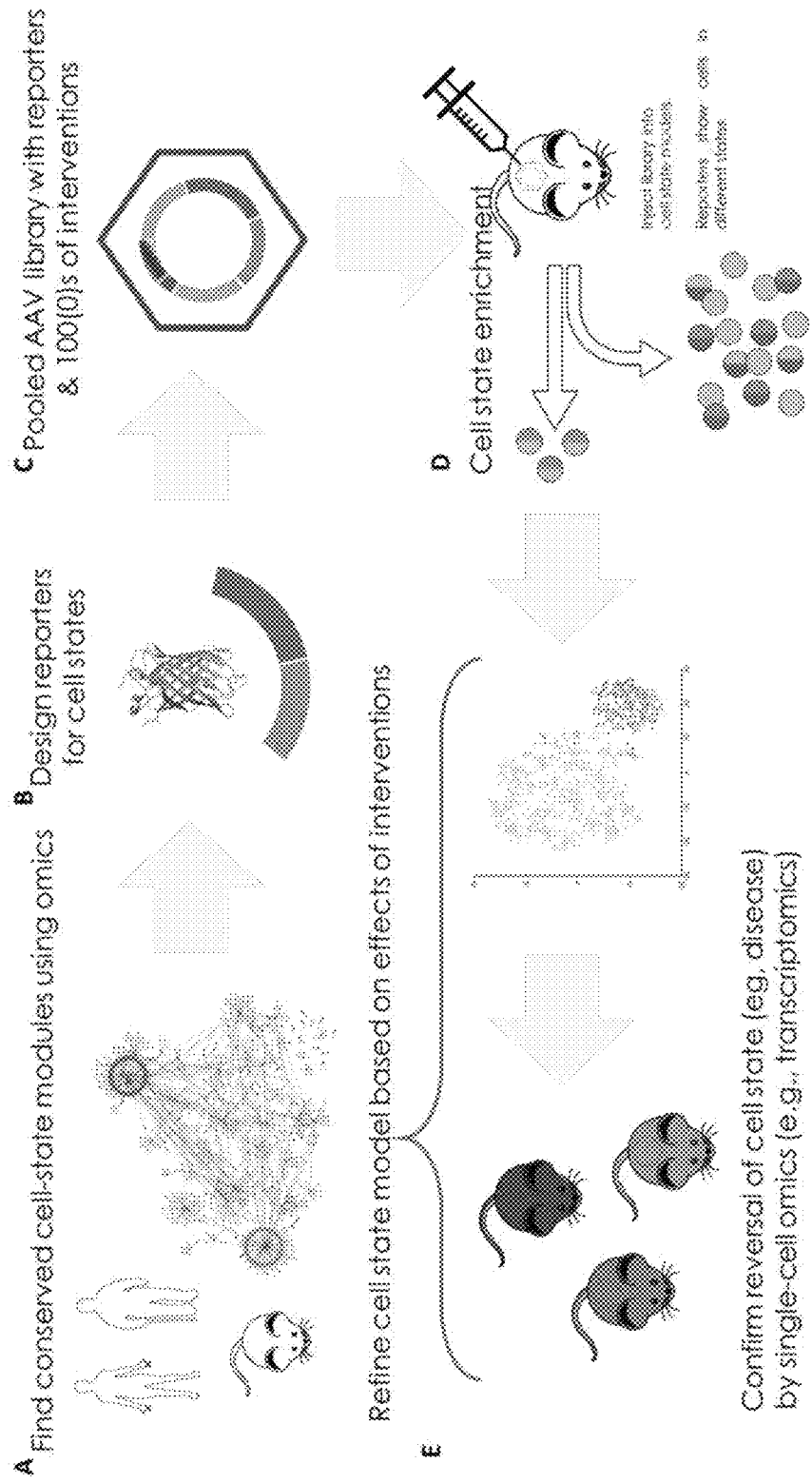
FIG. 1 illustrates a non-limiting example of a process of identifying candidate therapeutic moieties from libraries using the methods described herein, in certain embodiments of methods and compositions step (e) is replaced with spatial transcriptomics as described herein.

The present disclosure provides methods for in vivo screening of a plurality of therapeutic moieties. The compositions and methods herein can be used for unbiased in vivo screening of therapeutic moieties. Conserved disease models can be found, for example, using omics technology (panel A). Reporters can be designed for cell states within the conserved models (panel B). A vector library of nucleic acid sequences encoding for a plurality of therapeutic moieties (e.g., an AAV library), can be pooled with nucleic acid sequences encoding reporters for the cell state (panel C). Referring for example to FIG. 1, the present disclosure provides methods for in vivo screening of a plurality of therapeutic moieties. The cell state model can be refined based on the effects of therapeutic moieties.

Such methods provide a powerful alternative to traditional methods that require a known target, a priori knowledge or understanding of disease etiology, or analysis of one therapeutic moiety at a time. Advantages of the compositions and methods disclosed herein include, but are not limited to: no requirement for a priori knowledge or understanding of disease etiology, mechanism, or targets; a library or a plurality of different therapies or therapeutic moieties (e.g., at least 5, 10, 20, 50, 100, 200, 500, 1000, 10,000, or more than 10,000 therapies) can be screened at the same time (e.g., all in one biological entity) instead of one therapy at a time or using a large number of biological entities; screening in vivo allows one to capture or account for intracellular and extracellular factors, e.g., environmental factors, extracellular matrices, and complex interactions at the tissue, organic, or systemic level, including distal systemic interactions (such as the lymphatic system, circulatory system, or the immune system), that can impact a therapy or therapeutic moiety; high throughput screening in vivo facilitates translation from in vitro studies to in vivo therapies by accounting for various clinical factors, e.g., delivery, absorption, metabolism, pharmacokinetics, pharmacodynamics, and/or immune responses that affect effectiveness, efficacy, and/or safety of a therapy or therapeutic moiety. In some cases, screening a plurality of therapeutic moieties in one biological entity increases efficiency, consistency, and allows for side-by-side comparisons between different therapeutic moieties. Such in vivo screening decreases the number of biological entities required for a study.

The compositions and methods of use thereof disclosed herein allow one to conduct high throughput screening of a plurality of different therapeutic moieties in vivo. In some cases, such in vivo screening allows one to screen different therapeutic moieties in combination with a plurality of in vivo parameters, from administration or delivery to therapeutic effect, in one screen instead of one parameter at a time. For example, the present disclosure provides compositions and methods of use thereof for screening a library of different AAVs encoding a plurality of different therapeutic moieties at different doses, injected in different ways, and therapeutic moieties that interact with different targets in vivo. Steps of any method disclosed herein can be reiterated, each time with an optimized or a smaller pool of candidate therapeutic moieties than a previous round of screening.

In traditional methods, screening is often based on known targets and known effects, which is not always possible when the diseases or conditions are complex, involve multiple targets and pathways, and/or are of poorly understood mechanisms. Conventional screening methods are often time consuming, requiring separate analyses for different parameters, such as separate assays for targeting of a therapy to a target tissue or cell type of interest, separate assay for safety and adverse effects, separate assays for different doses, separate assays for each therapeutic moiety, and separate assays for preclinical analyses wherein each therapeutic moiety is administered separately, etc. This approach makes it impractical or too costly and time consuming to screen a large number of different therapeutic moieties, such as at least 50, at least 100, at least 200, at least 500, at least 1000, or at least 5000 therapeutic moieties. Such traditional target-based screening approaches often rely on biological hypotheses based on limited knowledge of a pathway derived from in vitro or ex vivo experiments, which probe limited aspects of cellular dysfunction and cannot be fully validated until tested in vivo. Not accounting for the in vivo factors, such as intracellular and extracellular factors, environmental factors, cell-to-cell interactions, cell-to-tissue and tissue-tissue interactions, tissue-to-organ interactions, different levels of matrices, microbiome environment, immune responses, and/or systemic, circulatory, or distal interactions (e.g., lymphatic system) in an animal or in vivo, conventional methods of screening and/or identifying therapies fail to capture how these factors impact a therapy, much less a library of different therapeutic moieties.

Further, a priori knowledge of a target in conventional drug discovery or therapy design can be limiting, as many diseases or conditions associated with ageing are complex and are poorly understood. The present disclosure provides an in vivo screen that relies on differences in cell states or a change in a cell state, which allows for screening of therapeutic moieties even where disease etiology is not known or not well understood. Such an in vivo screen and methods of use thereof provides a powerful tool for screening and identifying therapeutic moieties and methods of treatment without a need for a priori knowledge of therapy targets and/or mechanism.

Such compositions and methods of use thereof, as described herein, allow for high throughput in vivo screening of multiple therapeutic moieties at the same time and/or within a biological entity (e.g., an animal or organoid). Such high throughput in vivo screening can provide more consistent data and facilitate or expedite drug discovery and/or translation into clinical therapies with greater safety and/or efficacy in vivo.

The present disclosure provides an unbiased in vivo screening method comprising screening a plurality of candidate therapeutic moieties based on a change in a cell state, wherein a change in a cell can be a change in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, a nucleomic profile, or any combination thereof resulting from a therapeutic moiety. In some cases, such screening can be repeated multiples time. In some cases, a screening is followed by a cycle of candidate therapeutic moiety selection and/or in vivo optimization, screening using a composition and/or method disclosed herein (for example, a high throughput screen performed directly in a disease model), and candidate optimization.

Figure 2:
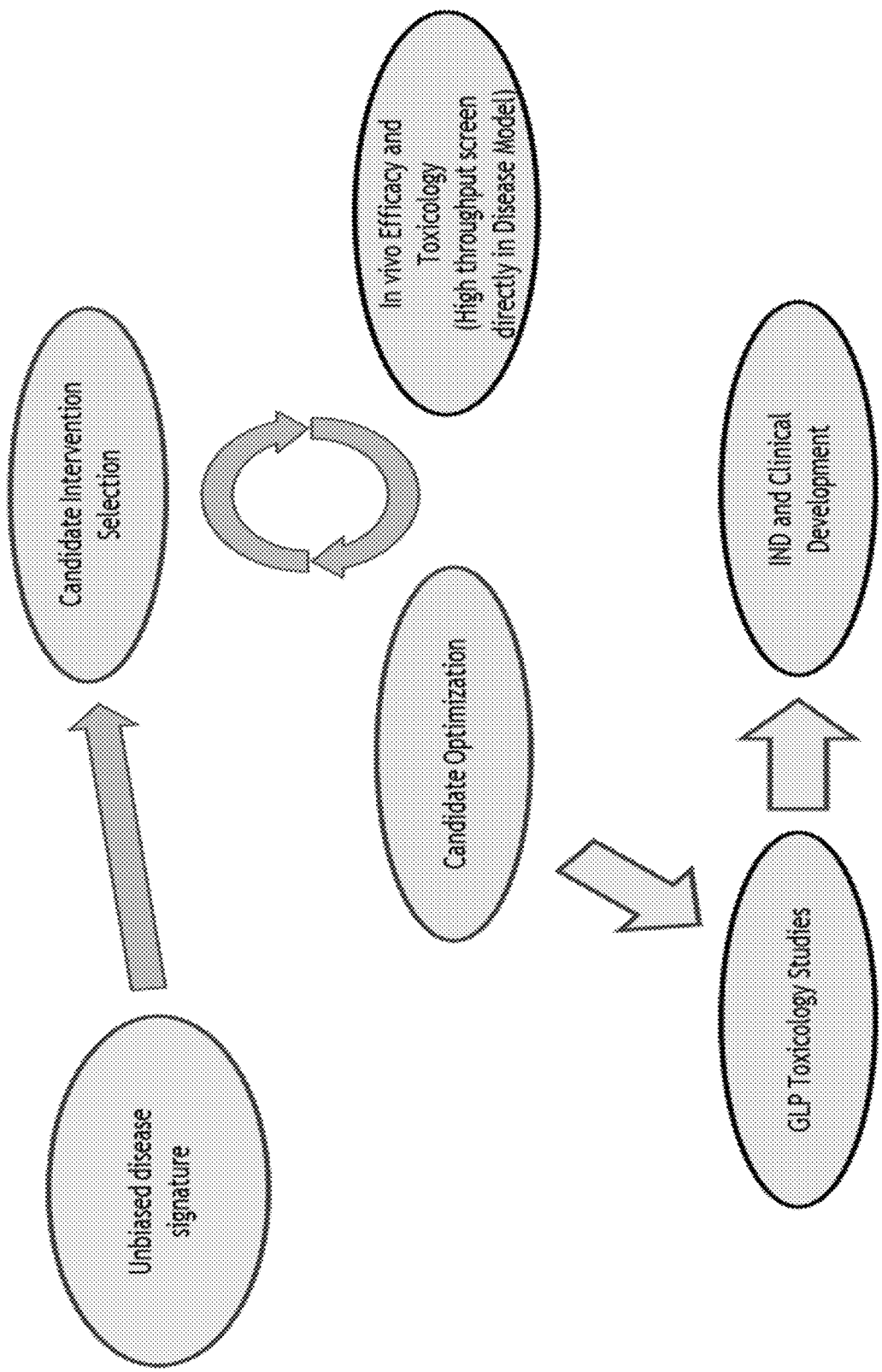
FIG. 2 illustrates a sample workflow for an unbiased in vivo screening method disclosed herein.

A schematic of an example of an in vivo screening workflow is illustrated in FIG. 2. For example, an unbiased disease signature, such as eigengene networks comprising co-expression modules, can be used to identify a plurality of different therapeutic moiety candidates, e.g., different therapeutic transgenes, for a disease or condition. Such library of different therapeutic moiety candidates can be screened in vivo using a high throughput screen disclosed herein to determine efficacy and/or toxicology of the candidate inventions. In some cases, toxicology can be determined through failure to identify specific therapeutic moieties (indicating cell death), or worsening of the disease signature. In some cases, one or more reporters are used to provide a therapeutic index corresponding to a desired change in a cell state resulting from a candidate therapeutic moiety in a cell or in contact with a cell. In some cases, candidates with positive therapeutic indices are further optimized. In some cases, the optimized candidates are screened one or more times to enrich for one or more candidate therapeutic moieties with a high therapeutic index, or high likelihood of resulting in a desired change in a cell state relative to the disease signature. This process of optimization and in vivo screening can be repeated. In some cases, optimized candidate therapeutic moieties are selected for further studies, e.g., good laboratory practice (GLP) toxicological studies, or injecting one of the optimized candidates into an animal for further analysis and/or validation. In some cases, optimized candidate therapeutic moieties derived from a screen disclosed herein can be further tested in clinical trials, such as an investigational new drug (IND). In some cases, data from an in vivo screen disclosed herein can be submitted as preclinical data in support of an IND application and clinical development.

An in vivo screening method can comprise a plurality of candidate therapeutic moieties identified from, derived from, or based on one or more disease signatures, e.g., a signature derived from one or machine learning methods, or one or more statistical methods, co-expression networks, differential expression signatures, eigengene networks, or a network comprising one or more co-expression modules. In some cases, an in vivo screening method disclosed herein is unbiased. In some cases, an in vivo screen disclosed herein comprises a plurality of different therapeutic moieties, wherein one or more therapeutic moieties results in a perturbation in a cell state.

An in vivo screening method can be capable of probing or assaying the perturbation on both intrinsic and extracellular factors including, but not limited to, interactions at the tissue, organ, and systemic level. In some cases, such perturbation results in a change in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, a nucleomic profile, a microbiomic profile, or any combination thereof resulting from a therapeutic moiety in the cell.

Unbiased in vivo screening methods can be used to screen for disease. Implementation of this method can find a conserved disease signature. In some cases, a library can be pooled with up to thousands of barcoded therapeutic moieties. In some cases, a library can be introduced into compelling disease models. In some cases, the disease signature and library design can be refined based on the effects of therapeutic moieties. Sequencing can test for reversal of disease state by each therapeutic moiety. In some cases, saturating treatment with top hits from the library can test toxicity and confirm therapeutic efficacy of hits. In some cases, clinical development can proceed in larger mammals, including extensive toxicity studies and clinical trials.

As used herein, a therapeutic moiety can comprise genetic material, a modulator of genetic material, or genetic material coding for a modulator of genetic material which can yield a therapeutic result when introduced to a subject with a disease or a condition or a model of a disease or condition.

Methods described herein can be used for a number of health and disease states, which can include states with a complex disease etiology, but strong evidence for a cell type to target for therapeutic effect. The method can be used on a sample group comprising patient samples and animal models. In some cases, an ideal animal model, which very closely mirrors a human disease or health state, can be used. The methods described herein can be applicable to age related and non-age-related disease and health states.

The term "expression" refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

An "expression cassette" refers to a nucleic molecule comprising one or more regulatory elements operably linked to a coding sequence (e.g., a gene or genes) for expression. In some aspects, an expression cassette may include a nucleic acid sequence encoding a therapeutic moiety. In some cases, the therapeutic moiety is operably linked to a therapeutic moiety barcode. In some aspects, an expression cassette may include a nucleic acid sequence encoding one or more reporters. In some cases, the sequence encoding a therapeutic moiety and the sequence encoding the one or more reporters may be on the same expression cassette. In other cases, the sequence encoding the therapeutic moiety and the sequence encoding the one or more reporters may be on different expression cassettes.

As used herein, "operably linked", "operable linkage", "operatively linked", or grammatical equivalents thereof refer to juxtaposition of genetic elements, e.g., a promoter, an enhancer, a polyadenylation sequence, etc., wherein the elements are in a relationship permitting them to operate in the expected manner. For instance, a promoter is operatively linked to a coding region if the promoter helps initiate transcription of the coding sequence. There may be intervening residues or elements between the promoter and coding region, such as an enhancer, so long as this functional relationship is maintained.

As used herein, the terms "treat", "treatment", "therapy" and the like refer to obtaining a desired pharmacologic and/or physiologic effect, including, but not limited to, alleviating, delaying or slowing progression, reducing effects or symptoms, preventing onset, preventing reoccurrence, inhibiting, ameliorating onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, e.g., arresting its development; and (c) relieving the disease, e.g., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

A "vector" as used herein refers to as any vehicle that can be used to mediate delivery of a nucleic acid molecule into a cell where it can be replicated or expressed. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Examples of vectors include plasmids and viral vectors. In some embodiments, a vector as used herein is a stable exosomal/non-integrating DNA vector.

As used herein, "therapeutic moiety", "therapeutic agent", and similar equivalents are used interchangeably to refer to any moiety or agent having a therapeutic effect on a cell or a cell state. A therapeutic moiety can include, but is not limited to, a biologic, a therapeutic transgene or products thereof (e.g., proteins), an enzyme replacement, a DNA sequence, an RNA sequence, an aptamer, an oligonucleotide, a polypeptide, shRNA, siRNA, miRNA, an antisense oligonucleotide, a morpholino, a protein degradation tag, a gene editing complex, a Cas fusion protein, CRISPRi, CRISPRa, an RNA editing element, a regulatory element of RNA splicing, an RNA degradation element, an epigenetic modification element, or any combination thereof. A "candidate therapeutic moiety" as used herein refers to any therapeutic moiety that has been identified as having a therapeutic effect or likely to have a therapeutic effect on a cell or a cell state (e.g., after screening a library of therapeutic moieties as provided herein).

A "reporter" as used herein refers to any sequence that can be directly or indirectly measured, preferably, although not necessarily, in a routine assay. In some embodiments, a reporter, as contemplated herein, is a reporter gene. A "reporter gene" as used herein refers to any sequence that produces a protein or peptide product that can be measured, preferably, although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest. In some cases, a reporter may be the protein product of a reporter gene.

The term "barcode," as used herein, generally refers to a label, or identifier, that conveys or is capable of conveying information about the analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time. In some cases, the barcode may be a therapeutic moiety barcode.

The term "transgene" as used herein includes any exogenous nucleic acid sequence that is artificially introduced into a cell or the genome of a cell. In some cases, a transgene can be an exogenous nucleic acid sequence that is naturally found in the cell in which it is being artificially introduced. In other cases, a transgene can be an exogenous nucleic acid sequence that is not naturally found in the cell in which it is being artificially introduced. In some cases, a transgene can comprise a gene or a portion of a gene. In some cases, a transgene may comprise one or more mutations relative to a wild-type nucleic acid sequence. In some cases, a transgene may comprise one or more regulatory elements, promoters, enhancers, activators, and the like. In some cases, a transgene may be a therapeutic transgene, meaning that a product of the transgene (e.g., a protein product) has or may have a therapeutic effect on the cell.

Further provided herein are kits comprising a plurality of therapeutic moiety expression cassettes, each comprising a nucleic acid sequence encoding a different therapeutic moiety operably linked to a therapeutic moiety barcode. In some cases, the plurality of therapeutic moiety expression cassettes further comprises a transcriptional activator or an inducer molecule. In some cases, the kit further comprises a plurality of reporter expression cassettes. The reporter expression cassettes may each comprise a nucleic acid sequence encoding one or more reporters. In some cases, the reporter expression cassettes may comprise an inducible transcriptional element linked to the sequence encoding the one or more reporters. In some instances, the transcriptional activator or inducer molecule may interact with, activate, or induce the inducible transcriptional element in each reporter expression cassette, such that the expression of the reporter is operably linked to expression of the therapeutic moiety as described herein. In some cases, the one or more reporters comprise one or more selection markers, detectable proteins, fluorescent proteins, cell surface markers, drug-sensitive selection markers, or inducible transcriptional elements. In some cases, the one or more reporters can be selected or optimized for a model of interest.

In some cases, a kit can comprise at least 10, 50, 100, 500, or 1000 different therapeutic moiety expression cassettes. In some cases, a kit can comprise at least 10, 50, 100, 500, 1000, or 10000 different therapeutic moieties (or nucleic acid sequences encoding therapeutic moieties). In some cases, the number of therapeutic moieties can be the same as the number of therapeutic moiety expression cassettes. In some cases, the number of therapeutic moieties can be greater than the number of therapeutic moiety expression cassettes. In some cases, the number of therapeutic moieties can be less than the number of therapeutic moiety expression cassettes.

In some kits, a therapeutic moiety expression cassette and a reporter expression cassette can be mixed together in one sample or supplied as separate samples. In some cases, mixing the expression cassettes in one sample can make the kit easier to use. In some cases, supplying the expression cassettes as separate samples can allow for modularity of the kit, allowing a mix and match approach. In some cases, supplying the expression cassettes as separate samples can allow the expression cassettes to be directed toward different tissues or regions in a model.

Further provided herein are methods for identifying a candidate therapeutic moiety comprising administering into a biological entity (e.g., an animal or organoid) a library of expression cassettes each comprising a nucleic acid sequence encoding a therapeutic moiety, and identifying a candidate therapeutic moiety that results in a change in a cell state or a likelihood of a cell state.

Identification of Conserved Cell-State Models

Methods can comprise identifying and/or employing a conserved model of disease or health. Conserved models can include any biological entity, including animal models, tissues, organoids, and cells, as described herein. Models can be a complete representation of a human disease or health state, or can represent a subset of features of a disease or health state. Models herein can comprise expression cassettes or libraries, and may be influenced by an expression cassette or library.

Disease signatures can be identified directly from patient or model tissues. Some disease signatures can be biomarkers. In some cases, therapeutic moiety testing can be performed directly in the patient or model tissues. Some methods can provide information regarding in vivo side effects of a candidate therapeutic moiety during screening.

A signal from a reporter can correlate to the likelihood of a cell state, allowing for differentiation between different cell states. A signal from a reporter can be distributed over space or time. In some cases, the signal is a fluorescent signal, a chemiluminescent signal, or a colorimetric signal. A fluorescence signal can be of a fluorescent protein, a fluorescent molecule which can be a binding partner of a reporter, or a molecule which, upon chemical interaction with the reporter, can produce a fluorescent signal. In some cases, there can be more than one reporter which can yield a signal. Differentiation can be based on a ratio of signals between different reporters, or based on an amount of reporters expressed in a population of cells. An amount of reporters can comprise a presence/absence determination, an absolute number of a reporter, or a relative number of a reporter. Differentiation can be based on detecting or counting the reporters in a population of cells.

Differentiation can correlate to a therapeutic index. In some cases, a therapeutic index can compare the amount of a therapeutic moiety to the amount of the therapeutic moiety which can cause toxicity. A therapeutic index can be based on a change in cellular parameter, a cellular activity or function, cell physiology, cell size, cell morphology, cell shape, a cell marker, cell density, a transcriptomic profile, a proteomic profile, an immunoproteomic profile, a pharmacogenomic profile, a nucleomic profile, or any combination thereof between different cell states. For example, in a model of type 1 diabetes, a change in a cellular activity or function can comprise an increase in insulin secretion of pancreatic beta cells. Differentiation techniques can be used to differentiate between cells having a therapeutic effect from a therapeutic moiety from cells having a toxic effect from a therapeutic moiety. In some cases, the ratio of signals between different reporters or the amount of reporters expressed in a population of cells can correlate to a therapeutic index, and may be indicative of a therapeutic effect resulting from a therapeutic moiety expressed in a cell.

Cell states can vary. In some cases, one or more cell states can be present in a cell, e.g., a proliferative cell state and a cancerous cell state. In some cases, several cell states can be present, e.g., 2, 3, 4, 5, 6, 7, 8, 9, or 10 cell states. In some cases, cell states can be, without limitation, a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, a non-cancerous cell state, a hyperplastic state, a non-hyperplastic state, a pluripotent state, a differentiated cell state, a non-differentiated cell state, a proliferative cell state, a non-proliferative cell state, a dysregulated cell state, a regulated cell state, an immune-reactive state, a non-immune reactive state, a dividing cell state, or a quiescent cell state. In some cases, a cell state can be associated with senescence, impaired cellular function, inadequate or imbalanced replication activity, an altered secretory phenotype, altered neuronal signaling, abnormal immunological activity, a misdifferentiated cell, an un-differentiated cell, or cancer.

A cell state can be a disease or condition or a state in which a cell has a disease or condition. A cell state can be a state in which a cell can be characterized by a disease or condition. A cell state can be healthy. A cell state can be a state in which a cell is associated with a disease or condition. In some cases, a disease or condition can be, without limitation, an age-related disease or condition, a liver disease or condition, a metabolic disease or condition, a cardiovascular disease or condition, a neurodegenerative disease or condition, an eye disease or condition, a degenerative disease or condition, an inflammatory condition, a fibrotic condition, an immunological condition, a skin condition, a hair condition, a nail condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease or dementia, or the disease or condition can be associated with senescence, inadequate or imbalanced replication activity, altered secretory phenotype, altered neuronal signaling, abnormal immunological activity, undifferentiated cell state, or cancerous.

In some cases, the likelihood of the cell state is statistically significantly greater than a random distribution, or the likelihood of the cell state is at least 50%, 55%, 60%, 65%, 70%, 75%, 80%, 85%, 90%, 95%, or 100%. In some cases, a cell state can comprise at least 5%, 10%, 20%, 30%, 40%, 50%, 60%, 70%, 80%, or 90% improvement or amelioration relative to a disease state, as measured by the cell's cellular parameter, cell physiology, transcriptomic profile, proteomic profile, metabolomic profile, epigenomic profile, proteogenomic profile, immunoproteomic profile, pharmacogenomic profile, or nucleomic profile relative to a disease state, or as measured by a reporter. For example, a cell of a model of Alzheimer's disease comprising a therapeutic moiety can exhibit fewer amyloid plaques than a cell of a model of Alzheimer's disease not comprising the therapeutic moiety.

Models of health and disease can be carefully chosen to ensure they mirror one or more human health or disease states. Conserved models of health and disease can be used by this platform for screening for disease signatures and for therapeutic moiety testing. Examples of disease models and health models include any biological entity, including a tissue, including human tissue, cultured cells, organoids, and animal models of disease and health states. Public data, sequenced patient samples from biobanks, or animal models and controls, or any combination thereof can be used to map characteristic transcriptional signatures of health or disease states.

A biological entity can be a tissue. The tissue can be a model of health or disease. A tissue can be live tissue, dead tissue, or fixed tissue. An example of a tissue which is implanted into an animal can be a xenograft of a human tumor cell into a mouse tissue. A tissue can be procured via biopsy, swab, or biological fluid sample. A tissue can be procured from live subjects or post mortem. A tissue can be procured from subjects having a disease, predisposed to a disease, susceptible to a disease, or who are apparently healthy. A tissue can be procured from subjects which consume water, food, or air of a particular type or from a particular source. A tissue can have a specified microbiome. A tissue can be grown, maintained, or differentiated ex vivo. A tissue can be fixed, fresh, or frozen at least once. If the model is a tissue, it can be procured from a subject that can be characterized as healthy or having, without limitation, an age-related disease or condition, a liver disease or condition, a metabolic disease or condition, a cardiovascular disease or condition, a neurodegenerative disease or condition, an eye disease or condition, a degenerative disease or condition, an inflammatory condition, a fibrotic condition, an immunological condition, a skin condition, a hair condition, a nail condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease or dementia, or the disease or condition is associated with senescence, inadequate or imbalanced replication activity, altered secretory phenotype, altered neuronal signaling, abnormal immunological activity, undifferentiated cell state, or cancerous.

A biological entity can be a cell or a population of cells. The cell or population of cells can be a model of health or disease. Examples include cells that can be implanted into an animal. An example of a cell model can be a tumor cell which can be injected into an animal as a model of tumor metastasis. In some cases, a cell model can be extracted from an animal. In some cases, a cell model can be a cell of human origin or a cell of non-human origin. In some cases, a cell can be a diseased cell or a non-diseased cell. In some cases, a non-diseased cell can be susceptible to disease, predisposed to disease, or previously diseased. In some cases, a non-diseased cell can be a healthy cell. A cell can be cultured in standard media, media containing additional nutrients, drugs, or toxins, media replete of a nutrient, drug, or toxin, a hypoxic environment, an anoxic environment, or a hyperoxic environment. In some cases, a cell may be of human or mammal origin.

A cell model can be co-cultured with another cell type. A cell model can be a differentiated or non-differentiated cell. If the model is a cell, it can be a genetically modified or non-genetically modified cell. In some cases, a cell can be characterized as being a cell that is healthy or a cell that is associated with an age-related disease or condition, a liver disease or condition, a metabolic disease or condition, a cardiovascular disease or condition, a neurodegenerative disease or condition, an eye disease or condition, a degenerative disease or condition, an inflammatory condition, a fibrotic condition, an immunological condition, a skin condition, a hair condition, a nail condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease or dementia, or the disease or condition is associated with senescence, inadequate or imbalanced replication activity, altered secretory phenotype, altered neuronal signaling, abnormal immunological activity, undifferentiated cell state, or cancerous.

In some instances, a biological entity can be an organoid. In some cases, the organoid is a model of health or disease. Non-limiting examples of organoids contemplated herein include brain organoids, liver organoids, pancreas organoids, and the like.

In some cases, a biological entity comprises an animal. In some cases, the animal is a model of health or disease. In some cases, an animal model is a mammal, a primate, a rodent, a mouse, a rat, a rabbit, a pig, a dog, a cat, or a monkey. In some cases, an animal is a humanized animal or a humanized mammal. In some cases, an animal is an animal characterized as having or is a model for a disease or condition disclosed herein. In some cases, the animal is a mouse or a mouse characterized as having or as a model for a disease or a condition disclosed herein, e.g., an age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease, or dementia, or a disease or a condition associated with senescence, inadequate or imbalanced replication activity, altered secretory phenotype, altered neuronal signaling, abnormal immunological activity, undifferentiated cell state, or cancerous.

Some animal models can have or can be characterized as having more than one disease or condition. Some animal models can have or can be characterized as having a disease which can be more severe, less severe, or about the same severity as the human disease or condition.

An animal can have a disease or condition, or can be predisposed to developing a disease or condition, or can be susceptible to contracting a disease or condition, or can be apparently healthy. In some cases, the animal can be a model for a disease or condition, or can be a model for predisposition to developing a disease or condition, or can be a model susceptible to contracting a disease or condition, or can be a model for apparently health. In some cases, an animal which is apparently healthy or is a model for apparently healthy can be free of a disease or condition, free of several diseases or conditions, or free of all diseases and conditions. Some animal models can model a disease in its entirety, and some animal models can model a portion of a disease.

Animal models can change phenotypically as the animal ages or grows. In some cases, animal models can be genetically modified animals. In some cases, animal models can be raised or maintained on a special diet, water, or air source. Some animal models can be germ free. Some animal models can be administered a toxin, vector, drug, or other moiety to induce a disease or health state. Some animal models can be wild type. In some cases, animal models can be genetically modified.

Conserved models of health and disease can allow analysis of not only individually affected genes, but can allow analysis of modules of co-regulated genes that are distinctive to a health and disease state. This can enable consistent comparative analyses, for example, in spatial transcriptomics. In some cases, conserved models of health and disease can be used to compare identified clusters within existing hypotheses about disease etiology, which can be based on gene ontology, and optionally, to correlate co-expression with intensity of disease pathology in tissue samples.

Figure 3:
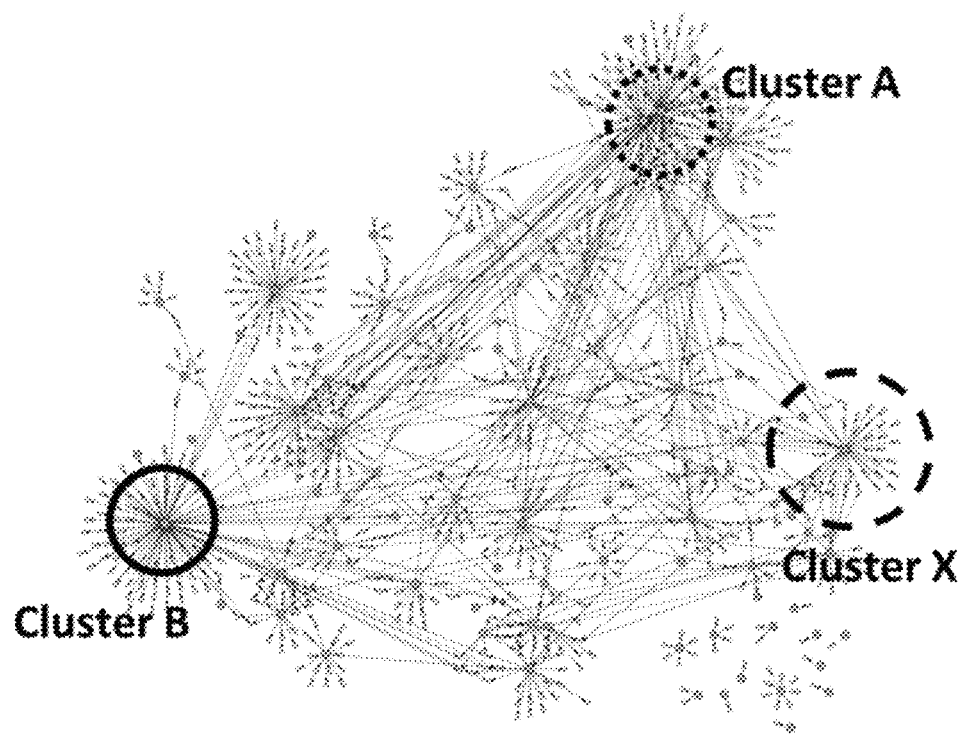
FIG. 3 illustrates an example of cluster analysis for the identification of genes associated with a disease.

For example, consider for a disease in a conserved model of disease a network of genes with clusters A, B, and X in FIG. 3. In this case, gene A can co-express with a large set of genes upregulated in the disease (cluster A, dotted circle), and gene B can co-express with a large set of genes downregulated in the disease (cluster B, solid line). In this example, gene A and gene B, as well as cluster A and cluster B, have orthologues that also co-express in the human disease. In this example, gene A or gene B can be potential targets for the disease. In this case, cluster X may also be observed. Upon analysis, it can become evident that cluster X co-expresses in the mouse model of the disease, but not in the human disease. In this case, cluster X can be ignored. Models of health and disease can provide a systems-level framework for drug discovery. For example, analysis in a model of epilepsy can identify Csf1R as a potential antiepileptic drug target.

A biological entity can comprise a library of therapeutic moieties as disclosed herein. The biological entity can be a model for or at risk for a disease or condition as described herein. In some cases, the biological entity is an animal. In some cases, an animal can be a mammal, a humanized disease model, or a mouse. The biological entity can express a therapeutic moiety, a reporter, or both, or the animal can be a carrier of one or more expression cassettes without expressing the genes therein.

Further provided in this disclosure are biological entities which can comprise a library of therapeutic moieties as described herein. A biological entity comprising a library of therapeutic moieties described herein can be healthy or diseased. A biological entity comprising a library of therapeutic moieties can have been administered a library of expression cassettes, each comprising a nucleic acid sequence encoding a different therapeutic moiety.

A biological entity expressing a library of therapeutic moieties can have been administered a library of expression cassettes by a local injection or a systemic injection or infusion. An injection herein can be an intravenous injection, an intramuscular injection, an intraocular injection, an intraarticular injection, an intravitreal injection, an intraretinal injection, an intraperitoneal injection, an intrahepatic injection, a subcutaneous injection, an intradermal injection, an epidural injection, a lymph node injection, an intracardiac injection, or any other type of injection.

A biological entity expressing a library of therapeutic moieties can have been administered at least 10, 50, 100, 500, 1000, or more different expression cassettes. A biological entity expressing a library of therapeutic moieties can have been administered a plurality of expression cassettes, wherein some or all of the expression cassettes comprise a nucleic acid sequence encoding a therapeutic moiety different from that of other expression cassettes in the library. A biological entity expressing a library of therapeutic moieties can have been administered a plurality of expression cassettes, wherein some or all of the expression cassettes comprise a therapeutic moiety barcode which is different from that of other expression cassettes in the library. A biological entity expressing a library of therapeutic moieties can have been administered a plurality of expression cassettes each comprising a nucleic acid sequence encoding different therapeutic moieties. A biological entity expressing a library of therapeutic moieties can have been administered a plurality of expression cassettes each comprising a different therapeutic moiety barcode.

In some instances, the biological entity expressing a library of therapeutic moieties can be an animal. Animals can be human or non-human. An animal which is non-human can be a mouse, a rat, a groundhog, a frog, a rabbit, a guinea pig, a hamster, a pig, a monkey, a horse, a squirrel, a fruit fly, a nematode, a dog, or a cat. In some instances, the biological entity expressing a library of therapeutic moieties can be a tissue, an organoid, a cell or a population of cells.

In a non-limiting example, a viral library of expression cassettes each comprising a nucleic acid sequence encoding different therapeutic moieties (e.g., RNAi), and expression cassettes comprising a nucleic acid sequence encoding one or more reporters, can be delivered to diseased tissue by local injection, in a group of mice which can comprise 5-10 mice. Control mice can be injected with constructs lacking RNAi therapeutic moieties or with scrambled RNAi, to eliminate reporter effects.

In another non-limiting example, a mouse model of osteoarthritis can receive an injection in the joint capsule of a library of expression cassettes comprising nucleic acid sequences encoding different therapeutic moieties which may improve osteoarthritis. Mice can be sacrificed, and the joint capsule tissue can be harvested and prepared to be placed on the spatially labeled slide for identification. In some cases, minimizing the time from sacrifice to sequencing can reduce noise from responses to the ex vivo environment.

In another non-limiting example, an adeno-associated virus (AAV) library of expression cassettes comprising nucleic acid sequences encoding different therapeutic moieties can be injected into a mouse model of glioblastoma. The injection can be either to the primary tumor directly, or an intravenous injection such that the library can reach metastases. After delivery of constructs to the mice, cells of the desired type (cancerous, non-cancerous, metastatic, cured, etc.) can be extracted and identified.

Candidates from analysis of therapeutic moieties can be transferred to preclinical testing of efficacy and safety. In some cases, genetic therapeutic moieties and expression cassettes can be compatible with clinical development. In some cases, the library can comprise hits, wherein hits can include one or more therapeutic moieties which can elicit a therapeutic response in a model. In some cases, exchanging a library for a single therapeutic moiety, or eliminating one or more reporters can increase compatibility with clinical development. In some cases, exchanging a library for a single therapeutic moiety and eliminating the reporters can increase compatibility with clinical development. In some cases, delivery, promoter strength, or specificity, or a combination thereof can be optimized for clinical development. In some cases, hits can be targeted by other modalities. For example, other modalities can include CRISPRi, CRISPRa, novel screens for small molecule or biological compounds, or drug repurposing. Analysis of therapeutic moieties can be transcriptomic, metabolomic, proteomic, epigenomic, proteogenomic, immunoproteomic, pharmacogenomic, or nucleomic analysis, or any combination thereof.

In another non-limiting example, a virus titer can be optimized for high coverage of diseased tissue, with limited multiplicity of infection. Relevant preclinical outcomes can be evaluated. Examples of relevant preclinical outcomes can include range of motion and improved histology scoring of joint cartilage structure in a model of osteoarthritis. In some cases, immunogenicity of AAVs or other vectors or other safety concerns can be evaluated. Some methods provided herein can lead to discovery of genetic cures, treatments, or therapies for complex diseases, including progressive or age-related diseases through identification of a candidate therapeutic moiety. Some methods can identify a candidate therapeutic moiety for a disease or condition which comprises a broad decline in physiology, poorly understood mechanisms, or multiple interconnected dysfunctions of various cells or tissues.

Diseases or conditions herein can comprise a disease or condition wherein their extracellular environment changes over space or time which affect the disease or condition, including diseases or conditions wherein reverting the extracellular environment can be therapeutic for the disease or condition. Some methods can provide a candidate therapeutic moiety for a disease or condition comprising one or more dysfunctions of one or more cells or tissues. In some cases, dysfunctions comprise altered intercellular communication, genomic instability, telomere attrition, epigenetic alterations, loss of proteostasis, deregulated nutrient sensing, mitochondrial dysfunction, cellular senescence, or stem cell exhaustion.

In some cases, one or more libraries are administered to a biological entity of this disclosure via local injection, e.g., injection in an organ or tissue of interest. In some cases, one or more libraries of this disclosure is administered via injection or infusion.

Reporter Design

Methods provided herein can comprise designing one or more reporters for cell states within a conserved cell state model. Reporters can be positive reporters or negative reporters. A reporter can be transcribed when a therapeutic moiety expressed from an expression cassette has a positive effect, has no effect, or has a negative effect. Some reporters can be operably linked to one or more enhancers or reporters or one or more additional reporters.

Reporters can be capable of differentiating cancerous cells from non-cancerous cells. In some cases, a library comprising one or more reporters is capable of differentiation between 2, 3, 4, 5, 6, 7, 8, 9, 10, or more cell states. Such differentiation can comprise detecting or measuring a change or a difference in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof.

A reporter can be used to identify cells which have been affected by a therapeutic moiety. In some cases, the reporter and the therapeutic moiety can be expressed from the same expression cassette, or from different expression cassettes. In some cases, an expression cassette can encode more than one reporter. In some cases, one or more reporters are indicative of a change in a cell state.

An expression cassette can comprise a promoter driving expression of the reporter. A reporter construct can further comprise two or more promoters, wherein the two or more promoters can be the same or different. A promoter can be a cognate promoter of a gene known to be downregulated or upregulated in a cell state. A cognate promoter can be an interacting set of more than one promoter. Activation or deactivation of the more than one promoter can induce transcription of the reporter. In some cases, expression of a reporter is indicative of a change in cell state when a cell-state specific promoter is used to drive expression of a reporter gene, such as a detectable protein or mRNA. In such cases, expression of the reporter gene indicates a likelihood of the cell state for which the promoter is specific or responsive to.

A reporter gene can be linked to a promoter. In some cases, different reporter genes can be linked to the same promoter, or to different promoters. A promoter can be a region of the expression cassette containing genetic material capable of initiating transcription of the reporter gene. In some cases, reporter genes can be linked to more than one promoter. In some cases, the promoter can further comprise an enhancer. An enhancer can be a region of the expression cassette containing genetic material which can increase the likelihood that transcription of the reporter gene will occur. In some cases, an enhancer can increase the likelihood of transcription upon interaction with a protein, e.g., an activator.

Reporters can comprise fluorescent proteins. For example, cell state reporters can comprise the common fluorescent proteins, green fluorescent protein (GFP) and/or red fluorescent protein (RFP). In some cases, fluorescent reporters can help identification of cells containing a therapeutic moiety. In some cases, fluorescent signal from the fluorescent protein can correlate to a likelihood of a cell state or a change from one cell state to a second cell state.

A reporter can be a selection marker, a detectable protein or oligonucleotide, a cell surface marker, a drug-sensitive element, an inducible element, or a fluorescent protein. Some reporters can comprise two or more reporters. In cases with two or more reporters, each reporter can be a different detectable protein or oligonucleotide, a different selection marker, a different fluorescent protein, or a different cell surface marker, or any combination thereof.

A reporter can be an RNA-based target for fluorescent in-situ hybridization probes. Some reporters can comprise two or more reporters. In cases of two or more reporters, each reporter can be a different targetable RNA sequence.

Reporters can be reporters of health status or state, disease, senescence, apoptosis, or other cell states. In some cases, cell state reporters can indicate the likelihood of disease or good health. In some cases, cell state reporters can confirm disease or good health. In some cases, cell state reporters can indicate correlation between a cell state and disease or health.

A cell state can be a disease or condition. In some cases, the disease or the condition is, without limitation, age-related disease or condition, a liver disease or condition, a metabolic disease, a cardiovascular disease, a neurodegenerative disease or condition, an eye disease or condition, a degenerative disease or condition, an inflammatory condition, a fibrotic condition, an immunological condition, a skin or hair condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease, or dementia. In some cases, the disease or the condition is associated with senescence, inadequate or imbalanced replication activity, altered secretory phenotype, altered neuronal signaling, abnormal immunological activity, undifferentiated cell state, or cancerous.

A cell state can be, without limitation, a diseased cell state, a non-diseased cell state, a healthy cell state, a normal cell state, an abnormal cell state, a senescent cell state, a metastatic state, a non-metastatic state, an apoptotic cell state, a non-apoptotic cell state, an infectious cell state, a non-infectious cell state, a cancerous cell state, or a non-cancerous cell state, a hyperplastic state, a non-hyperplastic state, a pluripotent state, a differentiated cell state, a proliferative cell state, a non-proliferative cell state, a dysregulated cell state, a regulated cell state, an immune-reactive state, a non-immune reactive state, a dividing cell state, a quiescent cell state, a cancerous cell state, or a non-cancerous cell state.

Figure 4:
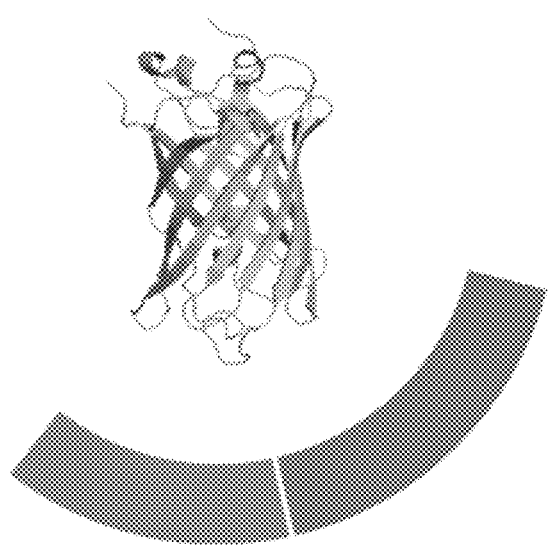
FIG. 4 illustrates a sample reporter for a disease module state.

A non-limiting example of a reporter protein is shown in FIG. 4. The arc represents the linear structure of the reporter construct, and comprises a promoter (left portion) and a fluorescent protein (right portion). The protein structure shown is a fluorescent protein which can be used as a reporter in libraries described herein.

In some cases, a reporter is a fluorescent protein capable of producing a fluorescent or a detectable signal upon a change. In some cases, a fluorescent signal is indicative of one cell state, e.g., a disease cell state. In some cases, a fluorescent signal is indicative of a second cell state, e.g., a normal cell state. In some cases, a change in a fluorescent signal or a ratio of fluorescent signals from different reporter proteins can be used to indicate a change in a cell state.

A change in a cell state or a change in the fluorescent signal of one or more reporters can be used to determine a therapeutic index based on a change in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, a nucleomic profile, or any combination thereof between different cell states. In some cases, a ratio between the different reporters or different fluorescent proteins or the amount of reporters expressed in a population of cells correlates to a therapeutic index, indicative of a therapeutic effect resulting from a therapeutic moiety expressed in the cell.

Reporters can be detected by their presence or absence, absolute value, relative value, normalized value, or binned value. In some cases, presence of a reporter can indicate health. In some cases, presence of a reporter can indicate a disease or an abnormal cell state. Reporter values for a given cell state can comprise a single value, a narrow range of values, or a broad range of values. Reporter values for a given cell state can vary based on the reporter molecule used. In some cases, a reporter comprises any detectable marker, e.g., a fluorescent protein or a cell surface marker. In some cases, a reporter comprises a drug-sensitive element or an inducible transcriptional element. In some cases, a reporter can be any marker or element that allows one to detect for spots containing cells comprising a therapeutic moiety that may have resulted in a therapeutic effect. In some cases, a reporter can be any marker or element that allows one to detect for spots containing cells with the same or similar cell state, or cells having the same perturbation or change resulting from a therapeutic moiety.

In some cases, an amount, a count, or a value of the reporters in a population of cells greater than random distribution can be indicative of a likelihood of a cell state in a population of cells. In some cases, the greater than random distribution can be statistically significant. In some cases, statistically significant can comprise a p value equal to or less than 0.1, 0.09, 0.08, 0.07, 0.06, 0.05, 0.04, 0.03, 0.02, 0.01, 0.001, 0.0001, 0.00001, or less.

In some cases, nucleic acid sequences encoding a reporter can be a range of sizes. Reporters can be less than 4000, 3500, 3000, 2500, 2000, 1500, 1400, 1300, 1200, 1100, 1000, 900, 800, 700, 600, 500, 400, 300, 200, or 100 base pairs in size. Promoters liked to the expression of reporters can also be a range of sizes. In some cases, each reporter gene can be between 700 and 1000 base pairs or between 1000 and 2000 base pairs in size. In some cases, the promoter can be no more than 100, 150, 200, 250, 300, 350, 400, 450, or 500 base pairs in size.

Expression of a reporter can be operably linked to an inducible transcriptional element that can be responsive to or linked to a transcription factor, wherein the transcription factor can comprise one or more therapeutic moieties, or wherein expression of the reporters is linked to expression of the therapeutic moieties. An inducible transcriptional element can be that of a cre-lox P system, myxovirus resistance 1 promoter, an estrogen receptor, optogenetics, ecdysone-inducibility, Gal4/UAS or tetracyclin off/on systems. In some cases, an inducible transcriptional element can allow for control of gene expression levels, temporal or spatial control of activation, or analysis of cellular gene dose/ response effects. In some cases, control of gene expression levels can prevent toxic effects on a cell from some gene products. In some cases, an inducible transcriptional element can prevent leakiness of the expression of a reporter.

In some cases, expression of one or more reporters can be operably linked to a transcriptional inducer or a transcriptional activator associated with a therapeutic moiety, such that expression of the therapeutic moiety induces or activates expression of the reporters.

In some cases, detection of a reporter can allow for differentiation between different cell states. For example, if a reporter expressed in a cell is linked to a promoter associated with Alzheimer's disease, then the cell can have or be a model of Alzheimer's disease. Reporters can allow for detection of cells with a disease or condition or cells lacking a disease or condition. Differentiation can be between diseased cell state and a healthy cell state, or between an abnormal cell state and a normal cell state. Differentiation between cell states can comprise a change or a detection of a change in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, or any combination thereof resulting from expression of a therapeutic moiety in a cell.

Expression Cassettes with Both Reporters and Therapeutic Moieties

The present disclosure provides libraries comprising a plurality of expression cassettes, each of the expression cassettes comprising a nucleic acid sequence encoding different therapeutic moieties. In some cases, a library of expression cassettes can be introduced, maintained, propagated, or administered to a biological entity. In some cases, a library of expression cassettes can be propagated in a cell or a population of cells, a cell line, or host cells.

Some libraries can comprise a plurality of expression cassettes. In some cases, the plurality of expression cassettes comprises a plurality of different expression cassettes. In some cases, each expression cassette comprises a nucleic acid sequence encoding a different therapeutic moiety. In some cases, each therapeutic moiety in a library is operably linked to a therapeutic moiety barcode. In some cases, each therapeutic moiety can be further linked to one or more reporters that collectively indicate a likelihood of a cell state. In some cases, a library comprising one or more reporters can collectively differentiate one cell state from another cell state, such as a diseased cell from a non-diseased cell state.

A library can comprise one or more reporters that are capable of differentiation between cell states. In some cases, such differentiation between two different cell states can be between a diseased cell and a healthy cell, or between an abnormal cell and a normal cell.

In some cases, a library comprising a plurality of therapeutic moieties further comprises one or more reporters capable of differentiating between cell states with an accuracy of at least 50%, 55%, 60%, 65%, 70%, 75%, 80%, 85%, 90%, 95%, or 100%. Some reporters can differentiate between cell states with precision of at least about 50%, 55%, 60%, 65%, 70%, 75%, 80%, 85%, 90%, 95%, or 100%.

Differentiation between cell states can be accomplished by a number of means. Means of differentiation between cell states can be selected for a particular reporter, therapeutic moiety barcode, or model. In some cases, the basis of differentiation between cell states can comprise a change in a cellular parameter, a cellular activity or function, cell physiology, cell size, cell morphology, cell shape, a cell marker, cell density, a transcriptomic profile, a proteomic profile, a metabolomic profile, an epigenomic profile, a proteogenomic profile, an immunoproteomic profile, a pharmacogenomic profile, or a nucleomic profile, or any combination thereof. In some cases, the basis of differentiation can be resulting from a therapeutic moiety in the cell. The differentiation can comprise a change in cellular activity or function, which includes, but is not limited to, transfection, transcription, replication, protein expression, epigenetic modification, cell marker expression, interaction with an exogenous molecule, or any combination thereof.

In some cases, a library comprising a plurality of expression cassettes further comprises a nucleic acid sequence encoding one or more reporters. In some cases, an expression cassette further comprises a promoter operably linked to a reporter gene. In some cases, a reporter gene further comprises an enhancer or repressor.

In some cases, a library of expression cassettes encodes a plurality of therapeutic moieties that are not physically linked to a reporter gene in the same expression cassette. In some cases, a library of expression cassettes comprises a plurality of expression cassettes, wherein each expression cassette encodes a therapeutic moiety and a reporter. In some cases, the reporter is encoded on a different expression cassette than the therapeutic moiety, or is located in trans relative to the therapeutic moiety. In some cases, a reporter gene is located in cis relative to a therapeutic moiety. In some cases, a reporter is encoded on the same expression cassette as a therapeutic moiety. In some cases, expression of a therapeutic moiety is linked, either in trans or in cis, to the expression of a reporter. In some cases, expression of a reporter is indicative of expression of a therapeutic moiety. In some cases, expression of a therapeutic moiety results in expression of a transcription factor, which activates transcription of a reporter in trans or in cis.

In some cases, a library of expression cassettes encoding a plurality of therapeutic moieties is pooled or mixed with a second library of expression cassettes encoding a plurality of different reporters. In some cases, a library of expression cassettes comprises expression cassettes encoding a plurality of different therapeutic moieties and one or more reporters. In some cases, the library of expression cassettes comprises the same reporter for all expression cassettes in a library (e.g., GFP) such that each cell of the biological entity expresses the same reporter. In some cases, different libraries can be pooled.

A therapeutic moiety can be used for a gene therapy. In some instances, the therapeutic moiety can be, without limitation, a DNA or RNA sequence, shRNA, siRNA, miRNA, an antisense oligonucleotide, a morpholino, a protein degradation tag, a therapeutic transgene or a product of a therapeutic transgene (e.g., a therapeutic protein), a gene editing complex, a Cas fusion protein, CRISPRi, CRISPRa, an RNA editing element, a regulatory element of RNA splicing, an RNA degradation element, or an epigenetic modification element. In some instances, the therapeutic moiety can comprise more than one therapeutic moiety. In some instances, the more than one therapeutic moiety can be encoded on the same expression cassette. In some instances, the more than one therapeutic moiety can be encoded on different expression cassettes. In some instances, the therapeutic moiety can be a protein. In some instances, the therapeutic moiety can comprise non-coding genetic material. In some instances, the therapeutic moiety can comprise both coding and non-coding genetic material.

Therapeutic moieties can be engineered based on transcriptomic signatures of a disease or a condition. In some methods, therapeutic moieties can be engineered based on a machine learning method, a statistical method, a neural network, a differential co-expression network, an interaction network, clustering, or gene set analysis. In some cases, transcriptomic signatures can further comprise a neural network of modules of co-regulated genes associated with a disease state. In some cases, a machine learning method, a statistical method, a neural network, a differential co-expression network, an interaction network, a clustering, or a gene set analysis can be used to modify one or more therapeutic moieties identified from an in vivo screen.

In some cases, the nucleic acid sequence encoding the therapeutic moiety and the nucleic acid sequence encoding the reporter can be packaged in the same vector. In some cases, the nucleic acid sequence encoding the therapeutic moiety and the nucleic acid sequence encoding the reporter can be packaged in separate vectors. When the sequence encoding the therapeutic moiety and the sequence encoding the reporter are packaged in separate vectors, reporter transcription can be dependent on transcription of the therapeutic moiety. In some cases, different vectors are pooled or mixed together before introducing into a biological entity for in vivo screening.

In some cases, the vector may be an AAV vector. In some cases, an AAV serotype may be chosen or developed for a known ability to infect a cell type of interest. In one example, three promoters of different strengths, with enhancer(s) to increase cell type specificity, plus a library of RNAi therapeutic moieties can be inserted into the AAV construct. Also inserted into the construct may be a fluorescent protein gene and a reporter promoter. In some cases, the fluorescent protein gene can be about 700 base pairs. In some cases, the reporter promoter can be about 300 base pairs. In some cases, the fluorescent reporter gene and reporter promoter together can comprise about half of the capacity of the AAV construct.

In some aspects, an expression cassette may comprise a barcode, or a nucleic acid sequence encoding a barcode. In some cases, the barcode can be a nucleic acid barcode, such as a DNA barcode or an RNA barcode. In some cases, a barcode can comprise a number of nucleotide bases. In some cases, barcodes can be nucleic acid sequences comprising at least 2, 3, 4, 5, 6, 7, 8, 9, or 10 bases. In some cases, each barcode in an expression cassette is unique from other barcodes in other expression cassettes. Each unique barcode can differ from other unique barcodes by at least 1, 2, 3, 4, 5, 6, 7, 8, 9, or 10 bases. A portion of the bases in some barcodes can be common to all expression cassettes. A portion of the bases in some barcodes can be common to some of the expression cassettes. A portion of the bases in some barcodes can be unique for each expression cassette. A portion of the bases in some barcodes can be unique for an expression cassette. All of the bases in some barcodes can be unique for each expression cassette. Some expression cassettes can have one barcode. Some expression cassettes can have more than one barcode. Some barcodes as described herein can be linked to a therapeutic moiety (e.g., a therapeutic moiety barcode) on a plurality of expression cassettes in a library.

In some cases, the barcode is a therapeutic moiety barcode. In some cases, the transcription of a therapeutic moiety barcode can be linked to the transcription of a therapeutic moiety. A therapeutic moiety barcode can be included in an open reading frame or not included in an open reading frame of the therapeutic moiety. In some aspects, a therapeutic moiety barcode can be directly attached to a therapeutic moiety. In some aspects, a therapeutic moiety barcode is not directly attached to a therapeutic moiety. In some instances, a therapeutic moiety barcode may be expressed from the same expression cassette as the therapeutic moiety, and may be under the control of the same promoter, or a different promoter. The transcript of the therapeutic moiety barcode and the transcript of the therapeutic moiety can be separate transcripts or a single transcript. In some cases, other components of the expression cassette can be linked to the transcription of the therapeutic moiety, the therapeutic moiety barcode, or both. Generally, the therapeutic moiety barcode is expressed in the same cell as the therapeutic moiety, such that the therapeutic moiety can be identified.

In some cases, the therapeutic moiety barcode may contain specific elements facilitating or permitting its amplification (e.g., by PCR) prior to or during sequencing, to increase the number of reads during sequencing or signal strength in other methods. In some cases, when a reporter and a therapeutic moiety are encoded on separate expression cassettes, each of the expression cassettes may comprise a barcode (e.g., a therapeutic moiety barcode and a reporter barcode). In some instances, the reporter barcode and the therapeutic moiety barcode can be different. In some cases, the reporter barcode and the therapeutic moiety barcode can be the same.

In some instances, therapeutic moiety barcodes may be unique for each therapeutic moiety. Put another way, each therapeutic moiety may be associated with its own unique therapeutic moiety barcode, such that the identity of the therapeutic moiety can be ascertained from identifying the therapeutic moiety barcode. In other instances, therapeutic moiety barcodes may be unique for each class or type of therapeutic moiety. Put another away, each class or type of therapeutic moiety may be associated with its own unique therapeutic moiety barcode, such that the class or type of therapeutic moiety can be ascertained from identifying the therapeutic moiety barcode. The therapeutic moiety barcodes can be nucleic acid barcodes (e.g., DNA or RNA barcodes). The therapeutic moiety barcodes can comprise a number of nucleotide bases. Therapeutic moiety barcodes can be nucleic acid sequences comprising at least 2, 3, 4, 5, 6, 7, 8, 9, or 10 bases. Each unique therapeutic moiety barcode can differ from other unique therapeutic moiety barcodes by at least 1, 2, 3, 4, 5, 6, 7, 8, 9, or 10 bases. A portion of the bases in some therapeutic moiety barcodes can be common to all therapeutic moieties, for example, to allow amplification. A portion of the bases in some therapeutic moiety barcodes can be common to some of the therapeutic moieties. A portion of the bases in some therapeutic moiety barcodes can be unique for each therapeutic moiety. A portion of the bases in some therapeutic moiety barcodes can be unique for the corresponding therapeutic moiety. All of the bases in some therapeutic moiety barcodes can be unique for each therapeutic moiety.

Any machine learning technique and/or statistical method can be used to identify candidate therapeutic moieties used in a library disclosed herein. In some cases, machine learning techniques and/or statistical methods are used to optimize previously screened therapeutic moieties. A machine learning technique and/or statistical method can comprise a neural network of modules of co-regulated genes associated with a disease state. In some cases, a machine learning technique and/or statistical method comprises a neural network, a differential co-expression network, an interaction network, a clustering, or a gene set analysis to modify a therapeutic moiety identified from the in vivo screen. In some cases, an eigengene network comprising co-expression modules is used to identify candidate therapeutic moieties and/or to optimize therapeutic moieties disclosed herein.

Data can become part of a genome-wide co-expression map of a diseased state. This data can be collected using transcriptomes from each perturbation as a primary input, and gene ontology or other public data as a secondary input. This can allow machine learning to predict the effects of therapeutic moieties or combinations of therapeutic moieties in vivo.

From a list of eigengenes comprising signature modules in a given disease and cell type, genes can be chosen for which there can be existing knowledge of promoter regions. This knowledge of the promoter regions can accelerate optimization. The promoters of these genes can be fused with fluorescent proteins.

Methods described herein can be implemented by machine (e.g., computer processor) executable code stored on an electronic storage location of a computer system. The machine executable or machine-readable code can be provided in the form of software. During use, the code can be executed by a processor. In some cases, code can be retrieved from a storage unit and stored on a memory unit for ready access by a processor. In some situations, an electronic storage unit can be precluded, and machine-executable instructions can be stored on a memory unit.

For a particular disease and cell type, there can be gene modules, which are groups of genes which are highly connected and may provide biological insights, which can be analogous to the clusters described herein. In some embodiments, gene modules may be represented as a list of eigengenes.

Bioinformatic analysis, which can comprise weighted gene co-expression network analysis, can provide a list of eigengenes for signature modules in a given disease and cell type, where eigengenes can be the best summary of the standardized module expression data. The module eigengene of a given module can be defined as the first principal component of the standardized expression profiles. Module eigengenes can be used to correlate modules with clinical traits. For example, eigengenes can define robust biomarkers.

Eigengenes can be used as features in more complex predictive modules, including decision trees and Bayesian networks. Networks between module eigengenes (eigengene networks, or networks whose nodes can be modules) can be constructed. Genes may be correlated with eigengenes to identify intramodular hub genes within a given module. A sum of adjacencies with respect to module genes can be used to determine from eigengenes to identify intramodular hub genes within a given module. Network statistics can be used to test whether a module is preserved in another dataset.

For example, gene expression networks can be assembled, and therapeutic moiety barcodes as described herein can be identified in sequencing data. Multiple RNAs can be grouped for each target. Efficacy of each genetic perturbation can be evaluated by a weighted comparison of transcriptomes relative to healthy and diseased control cells, for instance by differential expression analysis. In some cases, differential expression analysis can comprise performing statistical analysis to discover quantitative changes in expression levels between experimental groups. In some cases, differential expression analysis comprises the calculation of an eigengene which can differentiate healthy and diseased cells.

Figure 5:
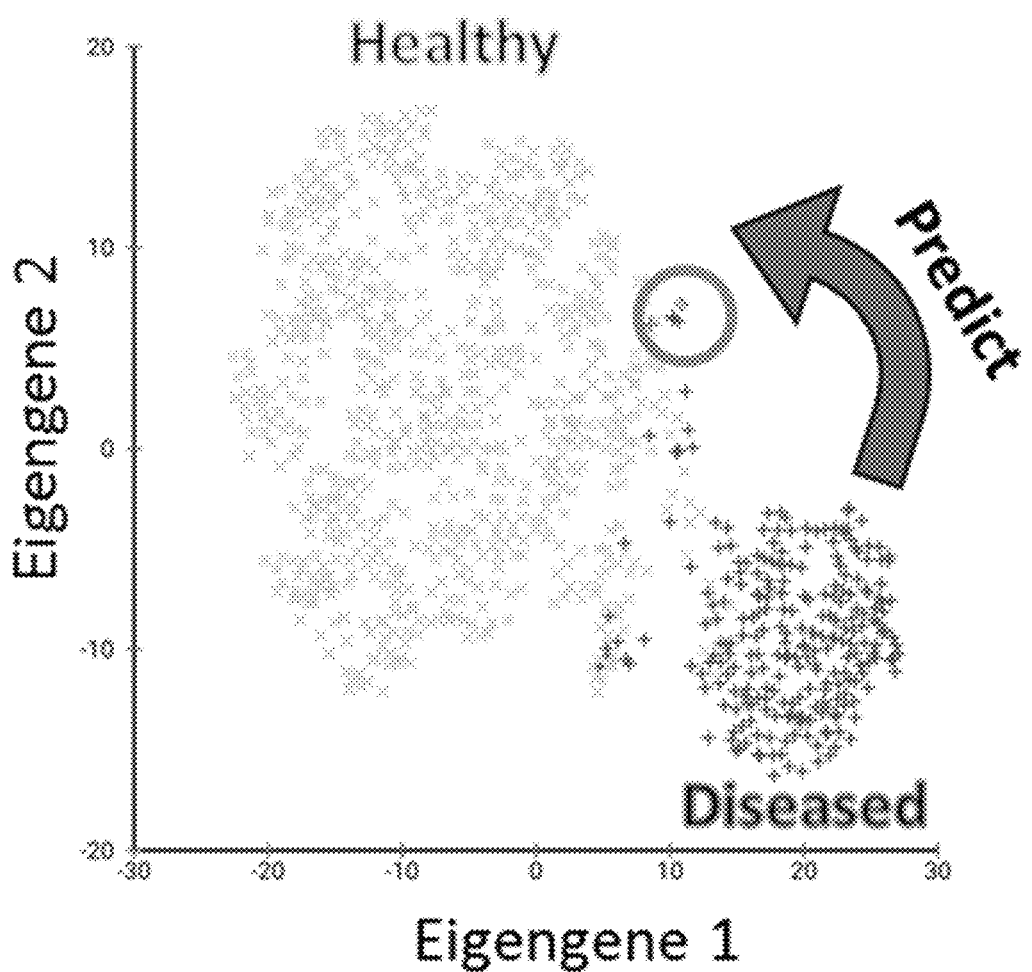
FIG. 5 illustrates an example of cell state analysis of single cells containing candidate therapeutic moieties in healthy vs. diseased models.
Figure 6:
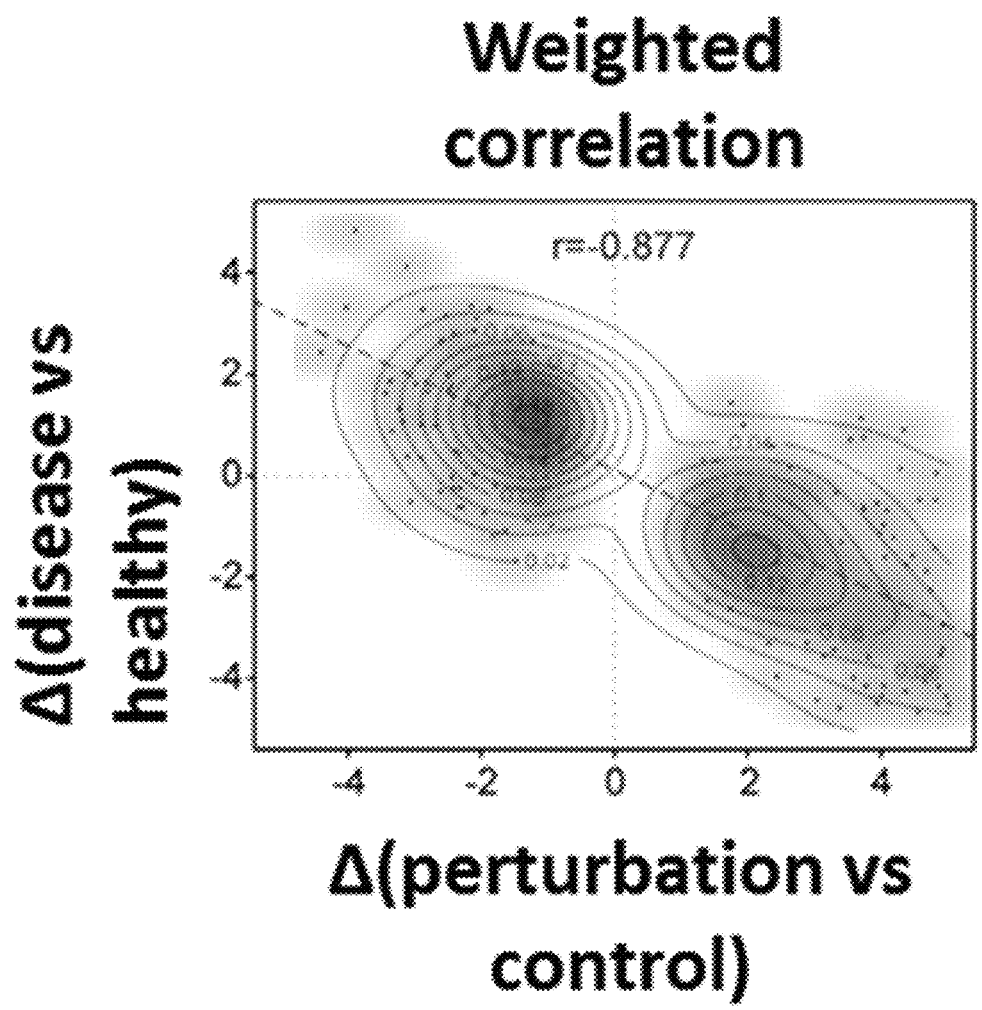
FIG. 6 illustrates a weighted correlation analysis of the effect of a genetic perturbation on a cell state.
Figure 7:
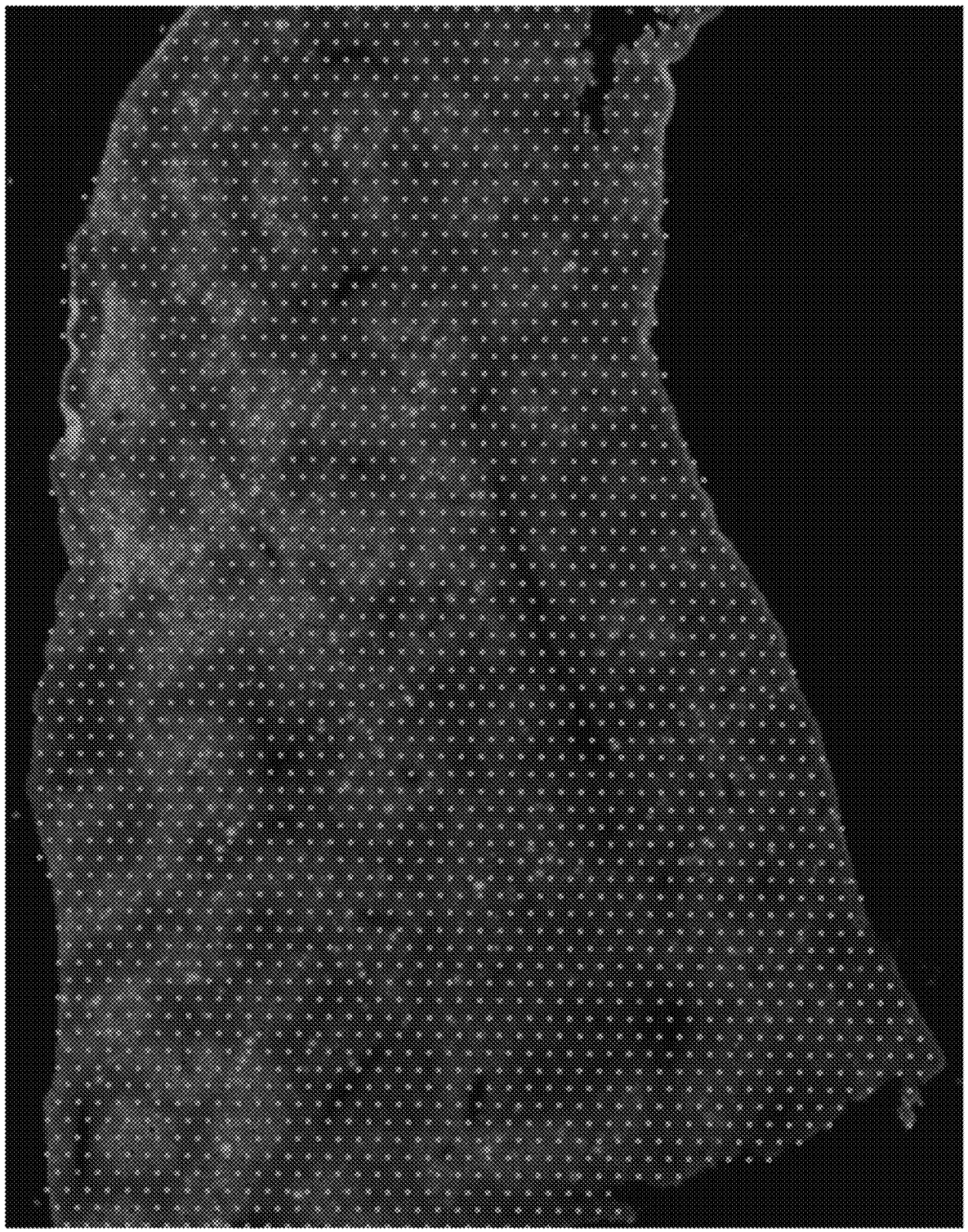
FIG. 7 illustrates an exemplary coupling of spatial and transcriptomic data in the form of 2d mapping, where dots represent coordinates on the glass slide, a specific therapeutic moiety barcode can be detected at these coordinated during RNA seq, and cells that express a given GFP promotor—which may or may not be an reporter of cell state-can be identified during the microscopy portion of analysis.

For example, as illustrated in FIG. 5, eigengene 1 and eigengene 2 represent two groups comprising co-expression modules: healthy and diseased. Each point corresponds to an RNAi, which can be associated with either a healthy cell or a diseased cell. In some cases, machine learning techniques can allow the prediction of which RNAi values could change upon administration of a therapeutic as part of an expression cassette as described herein.

As an example, this approach can be used to predict and validate effective reporters for the disease state in type I diabetes. Transcriptomic data from a type 1 diabetes disease model can be analyzed. These reporters can be delivered to the liver of mice which can be a conserved model of disease for type I diabetes. The behavior of these mice after administering known, effective therapeutics, for example insulin, can be measured.

A vector library can be pooled with reporters of therapeutic moieties. Vectors containing different therapeutic moieties can be gathered into a single library. Libraries can vary in size as described herein. Vectors within a vector library can all have the same reporter, or can have different reporters, or can have the same reporter with a different promoter or enhancer. Libraries can comprise one type of vector or more than one type of vector.

In some libraries, the plurality of expression cassettes can comprise at least 10, 100, 500, or 1000 different expression cassettes. Some libraries can comprise more than 1000 different expression cassettes. In some libraries, each different expression cassette can comprise a different therapeutic moiety. In some libraries, the plurality of expression cassettes can comprise at least 10, 100, 500, or 1000 different therapeutic moieties. Some libraries can comprise more than 1000 different therapeutic moieties.

In some libraries, expression cassettes can be packaged in a vector. Vectors can be of several types, delivered by several strategies, and formulated in a variety of formulations. The vector can be a viral vector or a non-viral vector. A viral vector can be an adeno-associated virus (AAV), a retrovirus, an adenovirus, or a lentivirus. A non-viral vector can be a linear vector, a plasmid, a polymer-based vector, a transposon, or an artificial chromosome.

In some cases, a non-viral vector can be delivered as a nanoparticle, a lipid nanoparticle, an RNA nanoparticle, or an exosome. A non-viral vector can be formulated for delivery using a physical method, a needle, a ballistic DNA, electroporation, sonoporation, photoporation, magnetofection, or hydroporation. A non-viral vector can be formulated for delivery with a chemical carrier, an inorganic particle, a metal nanoparticle, a magnetic nanoparticle, a lipid, a lipid nanoparticle, a peptide, a polymer, polyethylenimine (PEI), chitosan, polyester, dendrimer, or polymethacrylate.

In some cases, one or more chemical methods comprising an oligonucleotide, a lipoplex, a polymersome, a polyplex, a dendrimer, an inorganic nanoparticle, or a cell-penetrating peptide can be employed to enhance delivery of the vector. In some cases, a viral vector can be transfected as naked DNA. In some cases, two or more transfection methods can be combined as a hybrid method of transfection. For example, a virosome comprising a liposome with an inactivated virus can be employed for transfection. Other examples of hybrid methods of transfection can comprise a cationic lipid/virus hybrid or a hybridizing virus/virus hybrid. In some cases, transfection can be optimized to increase transfection levels or expression levels.

In some cases, an expression cassette encoding for the therapeutic moiety and an expression cassette encoding for the reporter can be packaged in the same vector or in separate vectors. When the expression cassette encoding for the therapeutic moiety and the expression cassette encoding for the reporter are packaged in separate vectors, reporter transcription can be dependent on therapeutic moiety transcription.

In some cases, an expression vector is used to deliver the nucleic acid molecule to a target cell via transfection or transduction. In some cases, a vector comprises an expression cassette.

A vector may be an integrating or non-integrating vector, referring to the ability of the vector to integrate the expression cassette or transgene into the genome of the host cell. Examples of expression vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs)); episomal vectors; transposons (e.g., PiggyBac); and (b) viral vectors such as retroviral vectors, lentiviral vectors, adenoviral vectors, and adeno-associated viral vectors.

Expression vectors may be linear oligonucleotides or circular plasmids and can be delivered to a cell via various transfection methods, including physical and chemical methods. Physical methods generally refer to methods of delivery employing a physical force to counteract the cell membrane barrier in facilitating intracellular delivery of genetic material. Examples of physical methods include the use of a needle, ballistic DNA, electroporation, sonoporation, photoporation, magnetofection, and hydroporation. Chemical methods generally refer to methods in which chemical carriers deliver a nucleic acid molecule to a cell and may include inorganic particles, lipid-based vectors, polymer-based vectors and peptide-based vectors.

An expression vector can be administered to a target cell using an inorganic particle. Inorganic particles may refer to nanoparticles, such as nanoparticles that are engineered for various sizes, shapes, and/or porosity to escape from the reticuloendothelial system or to protect an entrapped molecule from degradation. Inorganic nanoparticles can be prepared from metals (e.g., iron, gold, and silver), inorganic salts, or ceramics (e.g., phosphate or carbonate salts of calcium, magnesium, or silicon). The surface of these nanoparticles can be coated to facilitate DNA binding or targeted gene delivery. Magnetic nanoparticles (e.g., supermagnetic iron oxide), fullerenes (e.g., soluble carbon molecules), carbon nanotubes (e.g., cylindrical fullerenes), quantum dots, and supramolecular systems may also be used.

An expression vector can be administered to a target cell using a cationic lipid (e.g., cationic liposome). Various types of lipids have been investigated for gene delivery, such as, for example, a lipid nanoemulsion (e.g., a dispersion of one immiscible liquid in another stabilized by emulsifying agent) or a solid lipid nanoparticle.

An expression vector can be administered to a target cell using a peptide-based delivery vehicle. Peptide-based delivery vehicles can have advantages of protecting the genetic material to be delivered, targeting specific cell receptors, disrupting endosomal membranes and delivering genetic material into a nucleus. A vector can be administered to a target cell using a polymer-based delivery vehicle. Polymer-based delivery vehicles may comprise natural proteins, peptides and/or polysaccharides or synthetic polymers.

Further provided herein are methods for combinatorial examination of therapeutic moieties. To accomplish this, a library can be introduced as low coverage, infecting 0-10% of cells, to avoid or minimize multiplicity of infection in individual cells. Alternatively, a library could be introduced at higher coverage, such that several or many cells can contain multiple therapeutic moieties.

Multiple libraries or a multiple of the same library can be administered to a biological entity at separate time points. Promoters used for reporters in these cases can be designed to normalize expression for multiple infections. In one example, genes encoding multiple identifiable reporters (e.g., GFP and RFP) can be incorporated in different expression cassettes, each paired with a library of therapeutic moieties. In this example, cells of interest can contain multiple reporter colors, and the need to separate contributions of expression of a single reporter from each therapeutic moiety can be avoided.

Multiple therapeutic moieties can be combined in a single expression vector (based on disease signature, prior screens or other motivating information) to test for synergistic, additive or other combinatorial effects on cell states.

In Vivo Screening

In some aspects, the compositions and methods provided herein allow for in vivo screening of a library of therapeutic moieties. In some cases, in vivo screening involves screening a library of therapeutic moieties in a health or disease model. In some cases, in vivo screening involves screening a library of therapeutic moieties in a biological entity, such as, but not limited to, a cell or cell population (including cells or cell populations within living tissues, organisms, animals, organoids, and the like), a tissue, an organoid, or an animal. An expression cassette or library of expression cassettes can be administered into a model of health or disease such the model can then comprise the expression cassette or library. In such cases, the model (e.g., biological entity) can express the therapeutic moiety, the reporter, or both from the expression cassette. For example, a library of expression cassettes can be administered to a mouse model of a disease. In the model, one or more therapeutic moieties encoded by the library of expression cassettes can alter a cell state. Such an alteration can be reported by the reporter. For example, a fluorescent protein reporter can be transcribed and translated, upon a cell state change induced by a therapeutic moiety, and can allow for the detection or identification of an effective therapeutic moiety.

In one example, methods and compositions described herein can be applied to identify genes which can be therapeutic targets for an age-related disease. A biological entity (e.g., an animal or organoid) which is a model for the age-related disease, for example, an aged animal can be employed. The animal can be administered a library into a tissue which is affected by the age-related disease.

A library of therapeutic moieties can be administered to a model, wherein the model can be a conserved model for health and disease. In some cases, the model for health and disease is a biological entity, for example, a cell or population of cells, a tissue, an organoid, or an animal. Libraries can be administered topically, by injection, by washing, by ingesting, by implanting, by inhalation, sublingually, or by other methods. The biological entity can be a model of health or a model of an age-related disease or condition, a liver disease or condition, a metabolic disease or condition, a cardiovascular disease or condition, a neurodegenerative disease or condition, an eye disease or condition, a degenerative disease or condition, an inflammatory condition, a fibrotic condition, an immunological condition, a skin condition, a hair condition, a nail condition, a cancer, a type of arthritis, non-alcoholic fatty liver disease, non-alcoholic steatohepatitis, liver cirrhosis, idiopathic pulmonary fibrosis, sarcopenia, a neurological condition, Alzheimer's disease or dementia, or the disease or condition is associated with senescence, inadequate or imbalanced replication activity, altered secretory phenotype, altered neuronal signaling, abnormal immunological activity, undifferentiated cell state, or cancerous.

In a non-limiting example, an animal which is a model for Alzheimer's disease can receive an injection of a library into its brain. In another non-limiting example, an animal which is a model for type 1 diabetes can receive an injection of a library into its pancreas.

A library which is injected into a biological entity can comprise AAV vectors, each comprising a nucleic acid sequence encoding a reporter, a therapeutic moiety, and a therapeutic moiety barcode unique to the therapeutic moiety. Each of the vectors in the library can comprise a different therapeutic moiety. Such library can comprise at least 1000 different therapeutic moieties for screening in a biological entity.

Reporters in the library can be designed for a specific disease model. For example, reporters for a model of type 1 diabetes can be expressed in the presence of insulin. In this case, cells of the pancreas may express a therapeutic moiety which is effective in stimulating insulin production, and the insulin production can lead to expression of the reporter. In such methods, the expression of the reporter becomes a read-out for insulin production (and the therapeutic moiety that stimulated insulin production may be identified by identifying the therapeutic moiety barcode associated with that cell). Alternatively, reporters can be expressed in the presence or absence of other genes, which are not obviously disease related but are part of a disease signature previously identified. In a more general example, cells comprising a vector encoding a therapeutic moiety capable of treating the age-related disease can express a reporter.

Tissues or cells of the disease model can be harvested for analysis. For example, in an Alzheimer's disease model, the brain can be harvested. In another example, in a type 1 diabetes model, the pancreatic beta cells can be harvested.

Identification of Therapeutic Moieties

The strength (for example, degree of reduction of mRNA by RNAi or amount of mRNA transcript of a transgene) or amount of a therapeutic moiety present in a population of cells can be of interest. The strength or amount of a therapeutic moiety can give information, for example, about potency, toxicity, efficiency, or efficacy. In some methods, a candidate therapeutic moiety can be identified. In some cases, the identifying comprises RNA sequencing for an amount of a therapeutic moiety or a therapeutic moiety barcode in a population of cells, a histological assay, or a fluorescent staining assay to determine the amount of the therapeutic moieties present in the population of cells. In some cases, cell analysis can comprise Spatial Transcriptomic sequencing. Identifying can be quantitative or qualitative, and numerical results of identifying can be absolute or relative.

The likelihood of a cell state can correlate with a level of protein or oligonucleotide expression within a cell. In some cases, more protein or oligonucleotide expression can correlate with a more healthy or more diseased cell state. In some cases, less protein or oligonucleotide expression can correlate with a more healthy or more diseased state. In some cases, the level of protein or oligonucleotide expression can be measured using a histological or fluorescent staining method. Staining methods can comprise in situ hybridization, immunofluorescence, immunohistochemistry, Ponceau staining, Coomassie staining, silver staining, or other methods.

Specific Embodiments

In Addition to the Various Aspects and Embodiments Disclosed Elsewhere Herein, the Following embodiments are specifically contemplated:

1. A method for identifying a candidate therapeutic moiety comprising:
   (1) administering to an animal or an organoid a library of expression cassettes comprising:
      (a) a plurality of nucleic acid sequences, each encoding a different therapeutic moiety operably linked to a therapeutic moiety barcode; and
      (b) a plurality of nucleic acid sequences encoding one or more reporter constructs that collectively, when expressed in a cell, are indicative of a cell state or a likelihood of a cell state of the cell;
(2) removing a tissue from said animal or organoid and placing a section of said tissue on a coated surface; wherein said surface coating comprises primers encoding a spatial barcode providing coordinates for each of various spots on said coated surface;
(3) detecting a change in a cell state or likelihood of a cell state of one or more cells of the animal or the organoid and coordinating the presence of said therapeutic moiety to a specific cell or location within said tissue section using said spatial barcode, thereby identifying a candidate therapeutic moiety.

2. A method for identifying a candidate therapeutic moiety comprising:
(1) administering to an animal or an organoid a library of expression cassettes that include: (a) a plurality of nucleic acid sequences, each encoding a different therapeutic moiety operably linked to a therapeutic moiety barcode; and (b) a plurality of nucleic acid sequences encoding one or more reporters that collectively, when expressed in a cell, are indicative of a cell state or a likelihood of a cell state of the cell;
(2) removing a tissue from said animal or organoid and placing a two-dimensional section of said tissue on a coated surface; wherein the coating comprises oligo (dT) primers encoding a spatial barcode providing coordinates for each of various spots on said coated surface;
(5) permeabilizing the tissue on the slide;
(6) performing reverse transcription in said tissue section in situ to produce cDNA;
(5) performing RNA sequencing using the cDNA;
(6) identifying a candidate therapeutic moiety that results in the change in a cell state or likelihood of a cell state of one or more cells of the animal or the organoid; and coordinating the presence of the therapeutic moiety to a specific cell or location within the tissue section using the spatial barcode.

3. A method for identifying a candidate therapeutic moiety comprising:
(1) administering to an animal or an organoid a library of expression cassettes that include: (a) a plurality of nucleic acid sequences, each encoding a different therapeutic moiety operably linked to a therapeutic moiety barcode; and (b) a plurality of nucleic acid sequences encoding one or more reporter constructs that collectively, when expressed in a cell, are indicative of a cell state or a likelihood of a cell state of the cell;
(2) removing a tissue from said animal or organoid and placing a two-dimensional section of said tissue on a coated surface; wherein the coating comprises primers encoding a spatial barcode providing coordinates for each of various spots on said coated surface;
(3) identifying the location of therapeutic moieties through combined detection of therapeutic moiety barcodes and spatial barcodes;
(4) detecting a change in a cell state or likelihood of a cell state of one or more cells of the animal or the organoid using one or more selected from the group consisting of reporter constructs, histology, and transcriptomic analysis; and
(5) performing a weighted probability analysis to predict the likelihood of a cell state based on the cell's proximity to one or more therapeutic moieties in the tissue, thereby identifying a candidate therapeutic moiety.

4. The method of any of the preceding embodiments, wherein said tissue is permeabilized after being placed on a coating surface.
5. The method of any of the preceding embodiments, wherein reverse transcription is performed on nucleic acid in said tissue in order to produce cDNA.
6. The method of embodiment 4, wherein reverse transcription is performed on nucleic acid in said tissue in order to produce cDNA, RNA sequencing is performed on said cDNA, and wherein said RNA sequencing method comprises spatial transcriptomics.
7. The method of any of the preceding embodiments, wherein the level of protein or oligonucleotide expression is measured using immunohistochemistry or fluorescent in situ hybridization staining methods.
8. The method of embodiment 5, wherein said staining method utilizes fluorescent probes selected from GFP, RFP, or the like.
9. The method of any of the preceding embodiments, wherein said therapeutic moiety encodes for a secreted or cell-intrinsic signaling molecule involved in cell-cell signaling, or regulators thereof.
10. The method of any of the preceding embodiments, wherein said coated surface is a glass slide.
11. The method of any of the preceding embodiments, wherein said identifying comprises performing spatial transcriptomic RNA sequencing of a population of cells to determine an amount of the candidate therapeutic moiety present in the population of cells.
12. The method of any of the preceding embodiments, wherein the spatial barcodes in combination with the confirmed presence of a candidate therapeutic moiety allows mapping of the intervention's effect on all the cells contained within the specific spot, or adjacent spots, on the slide.
13. The method of any of the preceding embodiments, wherein each expression cassette of the plurality of expression cassettes is packaged in a virus.
14. The method of any of the preceding embodiments, wherein each expression cassette of the plurality of expression cassettes is packaged in an adeno-associated virus (AAV), adenovirus, or lentivirus.
15. The method of any of the preceding embodiments, wherein the change in the cell state or a likelihood of the cell state correlates to a therapeutic effect resulting from the candidate therapeutic moiety.
16. The method of any of the preceding embodiments, wherein the likelihood of the cell state correlates with a level of protein or oligonucleotide expression in the cell.
17. The method of any of the preceding embodiments, wherein the therapeutic moiety encodes for a secreted factor.
18. The method of any of the preceding embodiments, wherein the likelihood of the cell state is indicative to the cell receiving the candidate therapeutic moiety.
19. The method of any of the preceding embodiments, wherein the likelihood of the cell state is indicative of a nearby and/or neighboring cell receiving a candidate therapeutic moiety.
20. The method of any of the preceding embodiments, wherein the likelihood of the cell state is indicative of a cell receiving a secreted factor from a nearby and/or neighboring cell receiving a candidate therapeutic moiety.
21. The method of any of the preceding embodiments, wherein the therapeutic moiety barcode is between 1 and 12 nucleotides in length.

22. The method of any of the preceding embodiments, wherein the therapeutic moiety barcode is between 2 and 11 nucleotides in length.
23. The method of any of the preceding embodiments, wherein the therapeutic moiety barcode is between 4 and 10 nucleotides in length.
24. The method of any of the preceding embodiments, wherein the spatial barcode is 16 nucleotides in length.
25. The method of any of the preceding embodiments, wherein each of said spots on the slide comprises at least 1 cell.
26. The method of any of the preceding embodiments, wherein each of said spots on the slide comprises at least 2 cells.
27. The method of any of the preceding embodiments, wherein each of said spots on the slide comprises at least 3 cells.
28. The method of any of the preceding embodiments, wherein each of said spots on the slide comprises 4 cells.
29. The method of any of the preceding embodiments, wherein each of said spots on the slide comprises 5 cells.
30. The method of any of the preceding embodiments, wherein each of said spots on the slide comprises 6 cells.
31. The method of any of the preceding embodiments, wherein each of said spots on the slide comprises 7 cells.
32. The method of any of the preceding embodiments, wherein each of said spots on the slide comprises 8 cells.
33. The method of any of the preceding embodiments, wherein each of said spots on the slide comprises 9 cells.
34. The method of any of the preceding embodiments, wherein each of said spots on the slide comprises 10 cells.
35. A candidate therapeutic moiety identified by the method of any of the preceding embodiments.

EXAMPLES

Example 1: Constructing a Therapeutic Moiety Library

An pFB AAV plasmid suitable for viral packaging is used as a backbone for preparing a therapeutic moiety library. A common region for all therapeutic moieties is first cloned into this backbone, between the inverted terminal repeats used for AAV packaging. This common region contains: a CMV promoter, a hGH intro, and a green fluorescent protein-2A self-cleaving peptide. Next, specific regions for each therapeutic moiety are cloned in immediately downstream of the common region. These regions contain: the coding sequence of the therapeutic moiety (in this example, a transgene), a constant region serving as a PCR primer binding region for later steps, a therapeutic moiety barcode, a Tn7 sequence, and a polyadenylation sequence.

These plasmids are transfected into electrocompetent *E. coli*, cultured, and purified using ZymoPURE™ II Plasmid Midiprep kits (Zymo Research, manufacturer's protocol). The library is created by mixing the plasmids for each therapeutic moiety in equimolar ratios, and the resulting mixed plasmid is sent to the Harvard Vector Core for commercial production of AAV6.2 containing the mixed therapeutic moiety library.

Example 2: Library Delivery

An adult (8 weeks of age) hemizygous male mouse with the genotype B6N.Cg-Ids(tm1Muen)/J (A model for Hunter syndrome) is selected as a host for the therapeutic screen. The viral library is diluted in 1×PBS, to a final titer of $10^{11}$ viral genomes in 50 μL. After anesthetization using isoflurane, the virus is delivered by instillation using the protocol described in X. Su, M. Looney, L. Robriquet, X. Fang, and M. A. Matthay, "DIRECT VISUAL INSTILLATION AS A METHOD FOR EFFICIENT DELIVERY OF FLUID INTO THE DISTAL AIRSPACES OF ANESTHETIZED MICE," Exp. Lung Res., vol. 30, no. 6, pp. 479-493, January 2004. The mouse is observed after waking from anesthesia, and the following morning, to ensure that no adverse reaction to the viral delivery occurs.

Example 3: Tissue Isolation and Spatial Transcriptomics

The host mouse is sacrificed after a 4-week incubation period to allow expression of the library transgenes and certain organs are subjected to spatial transcriptomics, for examples using the methods as described in Stahl el al (Science Mag, 1 Jul. 2016, Vol 353 Issue 6294).

The host mouse as well as a non-injected mouse are sequentially anesthetized using isoflurane, sterilized with ethanol, and the abdominal cavity surgically opened to access the tissues of interest. The body is perfused with 10 mL of cold PBS through the left ventricle of the heart. The entirety of the tissues of interest are removed and flash frozen in liquid nitrogen. Spatial transcriptomics are performed generally in accordance with the manufacturer's instructions. The tissue is processed and sectioned into approximately 5 um thick section and then allowed to adhere to the 10× Genomics Visium Spatial glass slides. A permeabilization buffer is then applied to said tissue sections, to release mRNA from the cells. The glass slides contain spatially barcoded oligonucleotides, which bind to the mRNA released during the permeabilization stage. The bound mRNA is then subjected to reverse transcription in order to produce cDNA. Once a second strand of cDNA has been synthesized, it is denatured for downstream sequencing analysis and amplified per manufacturer's instructions (10× Genomics). During this process, part of the cDNA is separated and used to PCR amplify the therapeutic moiety barcodes prior to sequencing. The amplified barcode cDNA is loaded (95:5 ratio) to an Illumina Nextseq, using a 75-cycle high output kit per manufacturer's instructions. Upon completion of the sequencing run, another identical sequencing run is performed to add read depth.

Example 4: Data Analysis

Raw sequencing data is processed using bcl2fastq software (Illumina), aligned using STAR (A. Dobin et al., "STAR: ultrafast universal RNA-seq aligner," Bioinformatics, vol. 29, no. 1, pp. 15-21, October 2012) followed by SpaceRanger (10× Genomics) to assign reads to individual spots. A custom tool then maps therapeutic moiety barcode reads to individual spots, based on spatial barcodes detected in those reads. This results in groups of spots identifiable as having received a specific therapeutic moiety, including negative control therapeutic moieties without a transgene. Differential gene expression is compared across these groups to identify transcription effects of the therapeutic moieties. Additionally, a custom tool annotates additional spots by proximity to spots with interventions, and the differential gene analysis is repeated for these groups. Additionally, a Random Forest classifier previously trained on Hunter syndrome as well as healthy mouse single-cell data is applied to the groups of cells containing each therapeutic moiety. Where cells from this Hunter syndrome mouse are more likely to be classified as 'healthy', compared to negative control therapeutic moieties, therapeutic efficacy is indicated.

The inventions illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present inventions have been specifically disclosed by preferred embodiments and optional features, modification and variation of the concepts herein disclosed may be resorted to by those skilled in the art, and that such modifications and variations are considered to be within the scope of the inventions as defined by the appended claims and elsewhere in the disclosure.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of various aspects and embodiments of inventions contemplated herein.

Certain aspects and embodiments of inventions have been described broadly and generically herein. Each of the narrower species and subgeneric groupings falling within the generic disclosure also form part of some aspects and embodiments of inventions contemplated herein. This includes the generic description of inventions with a proviso or negative limitation removing any subject matter from the genus, regardless of whether or not the excised material is specifically recited herein.

In addition, where features or aspects of the invention are described in terms of Markush groups, those skilled in the art will recognize that some aspects and embodiments of inventions contemplated herein are also thereby described in terms of any individual member or subgroup of members of the Markush group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying a candidate therapeutic moiety comprising:
    (1) administering to an animal or an organoid a library of expression cassettes comprising:
        (a) a plurality of nucleic acid sequences, each encoding a different therapeutic moiety operably linked to a therapeutic moiety barcode; and
        (b) a plurality of nucleic acid sequences encoding one or more reporter constructs that alone or collectively are indicative of a cell state or a likelihood of a cell state of the cell;
    (2) removing a tissue from said animal or organoid and placing a section of said tissue on a coated surface; wherein said surface coating comprises primers encoding a spatial barcode providing coordinates for each of various spots on said coated surface;
    (3) detecting a change in a cell state or likelihood of a cell state of one or more cells of the animal or the organoid and coordinating the presence of said therapeutic moiety to a specific cell or location within said tissue section using said spatial barcode,
wherein detecting comprises performing spatial transcriptomic RNA sequencing of a population of cells to determine an amount of the candidate therapeutic moiety present in the population of cells, thereby identifying a candidate therapeutic moiety.

2. The method of claim 1, wherein said tissue is permeabilized after being placed on a coating surface.

3. The method of claim 2, wherein reverse transcription is performed on nucleic acid in said tissue in order to produce cDNA.

4. The method of claim 3, wherein reverse transcription is performed on nucleic acid in said tissue in order to produce cDNA, RNA sequencing is performed on said cDNA, and wherein said RNA sequencing method comprises spatial transcriptomics.

5. The method of claim 4, wherein a level of protein or oligonucleotide expression is measured in said tissue using immunohistochemistry or fluorescent in situ hybridization staining methods.

6. The method of claim 5, wherein said staining method utilizes fluorescent probes selected from green fluorescent protein (GFP), red fluorescent protein (RFP), or the like.

7. The method of claim 6, wherein said therapeutic moiety encodes for a secreted or cell-intrinsic signaling molecule involved in cell-cell signaling, or regulators thereof.

8. The method of claim 7, wherein said coated surface is a glass slide.

9. The method of claim 1, wherein the spatial barcodes in combination with the confirmed presence of a candidate therapeutic moiety allows mapping of the intervention's effect on all the cells contained within the specific spot, or adjacent spots, on the coated surface.

10. The method of claim 9, wherein each expression cassette of the plurality of expression cassettes is packaged in a virus.

11. The method of claim 10, wherein each expression cassette of the plurality of expression cassettes is packaged in an adeno-associated virus (AAV), adenovirus, or lentivirus.

12. The method of claim 11, wherein the change in the cell state or a likelihood of the cell state correlates to a therapeutic effect resulting from the candidate therapeutic moiety.

13. The method of claim 12, wherein the likelihood of the cell state correlates with a level of protein or oligonucleotide expression in the cell.

14. The method of claim 13, wherein the therapeutic moiety encodes for a secreted factor.

15. The method of claim 14, wherein the likelihood of the cell state is indicative to the cell receiving the candidate therapeutic moiety.

16. The method of claim 14, wherein the likelihood of the cell state is indicative of a neighboring cell receiving a candidate therapeutic moiety.

17. The method of claim 16, wherein the likelihood of the cell state is indicative of a cell receiving a secreted factor from a neighboring cell receiving a candidate therapeutic moiety.

18. A method for identifying a candidate therapeutic moiety comprising:
   (1) administering to an animal or an organoid a library of expression cassettes that include:
      (a) a plurality of nucleic acid sequences, each encoding a different therapeutic moiety operably linked to a therapeutic moiety barcode; and
      (b) a plurality of nucleic acid sequences encoding one or more reporter constructs that alone or collectively are indicative of a cell state or a likelihood of a cell state of the cell;
   (2) removing a tissue from said animal or organoid and placing a two-dimensional section of said tissue on a coated surface; wherein the coating comprises primers encoding a spatial barcode providing coordinates for each of various spots on said coated surface;
   (3) identifying the location of therapeutic moieties through combined detection of therapeutic moiety barcodes and special barcodes;
   (4) detecting a change in a cell state or likelihood of a cell state of one or more cells of the animal or the organoid using one or more selected from the group consisting of reporter constructs, histology, and transcriptomic analysis; and
   (5) performing a weighted probability analysis to predict the likelihood of a cell state based on the cell's proximity to one or more therapeutic moieties in the tissue, thereby identifying a candidate therapeutic moiety, wherein detecting comprises performing spatial transcriptomic RNA sequencing of a population of cells to determine an amount of the candidate therapeutic moiety present in the population of cells, thereby identifying a candidate therapeutic moiety.

* * * * *